United States Patent
Fukuda

(10) Patent No.: US 9,254,928 B2
(45) Date of Patent: Feb. 9, 2016

(54) LIQUID MEDICATION DISPENSING MACHINE

(75) Inventor: Yusuke Fukuda, Hirakata (JP)

(73) Assignee: TAKAZONO TECHNOLOGY INCORPORATED, Hirakata-shi (JP)

(*) Notice: Subject to any disclaimer, the term of this patent is extended or adjusted under 35 U.S.C. 154(b) by 383 days.

(21) Appl. No.: 13/824,189

(22) PCT Filed: Oct. 4, 2011

(86) PCT No.: PCT/JP2011/072856
§ 371 (c)(1),
(2), (4) Date: Mar. 15, 2013

(87) PCT Pub. No.: WO2012/046723
PCT Pub. Date: Apr. 12, 2012

(65) Prior Publication Data
US 2013/0174939 A1    Jul. 11, 2013

(30) Foreign Application Priority Data

Oct. 7, 2010  (JP) .................................. 2010-227717
Oct. 7, 2010  (JP) .................................. 2010-227718
Jan. 13, 2011  (JP) .................................. 2011-005033

(51) Int. Cl.
*B65B 3/04* (2006.01)
*A61J 3/00* (2006.01)
(Continued)

(52) U.S. Cl.
CPC . *B65B 3/04* (2013.01); *A61J 3/002* (2013.01); *B65B 3/003* (2013.01); *B67D 7/02* (2013.01);
(Continued)

(58) Field of Classification Search
CPC ............................ B65B 3/003; G06F 19/3462

USPC .......... 141/144–148, 284; 366/93, 96, 162.2, 366/187, 200, 209, 210, 211; 700/243; 222/167, 168
See application file for complete search history.

(56) References Cited

U.S. PATENT DOCUMENTS 2,056,014 A * 9/1936 Moore et al. .................. 366/209
5,078,302 A * 1/1992 Hellenberg .................... 222/144
(Continued)

FOREIGN PATENT DOCUMENTS

CN          2822754 Y    10/2006
CN        101165348 A     4/2008
(Continued)

OTHER PUBLICATIONS

Japanese Office Action dated Jul. 29, 2014, issued in corresponding Japanese Patent Application No. 2010-227717 with English translation (4 pages).
(Continued)

*Primary Examiner* — Timothy L Maust
(74) *Attorney, Agent, or Firm* — Westerman, Hattori, Daniels & Adrian, LLP

(57) ABSTRACT

A liquid medication dispensing machine capable of stirring a liquid medication contained in a liquid medication bottle in the machine with a simple structure is provided. The liquid medication dispensing machine supplying a liquid medication from a liquid medication bottle (23) containing the liquid medication to a prescription bottle includes a holder (78) holding a bottom (23B) of the liquid medication bottle (23), and a rotationally driving unit (61) generating rotary force and rotating the holder (78) and the liquid medication bottle (23) held by the holder (78) around a rotation axis (L3) extending along a center line (L2) of the liquid medication bottle (23).

16 Claims, 19 Drawing Sheets

(51) Int. Cl.
  *B67D 7/02* (2010.01)
  *B65B 3/00* (2006.01)
  *G06F 19/00* (2011.01)
  *G07F 17/00* (2006.01)
  *G07F 13/02* (2006.01)
  *G07F 13/06* (2006.01)

(52) U.S. Cl.
  CPC .......... *G06F 19/3462* (2013.01); *G07F 13/025* (2013.01); *G07F 13/065* (2013.01); *G07F 17/0092* (2013.01)

(56) References Cited

U.S. PATENT DOCUMENTS

| | | | |
|---|---|---|---|
| 5,353,665 A | | 10/1994 | Heebner |
| 5,947,337 A | * | 9/1999 | Worth .......................... 222/168 |
| 7,461,650 B1 | * | 12/2008 | Rand ........................ 128/200.23 |
| 7,631,783 B1 | * | 12/2009 | Laible ...................... 222/153.04 |
| 7,666,681 B2 | * | 2/2010 | Ammann et al. ............... 436/45 |
| 7,789,552 B2 | | 9/2010 | Girvin et al. |
| 2008/0260549 A1 | | 10/2008 | Yajima |
| 2010/0243103 A1 | | 9/2010 | Ono et al. |

FOREIGN PATENT DOCUMENTS

| | | |
|---|---|---|
| EP | 2 208 679 A1 | 7/2010 |
| JP | S63-071699 A | 4/1988 |
| JP | 06-40403 A | 2/1994 |
| JP | 2004-175415 A | 6/2004 |
| JP | 2007-014618 A | 1/2007 |
| JP | 2007-319383 A | 12/2007 |
| JP | 2008-056290 A | 3/2008 |
| JP | 2008-081135 A | 4/2008 |
| JP | 2009-112673 A | 5/2009 |
| JP | 2009-178495 A | 8/2009 |
| JP | 2009-268823 A | 11/2009 |
| JP | 2009-291248 A | 12/2009 |

OTHER PUBLICATIONS

Australian Office Action dated Sep. 18, 2014, issued in corresponding Application No. 2011313320; (5 pages).
Chinese Office Action dated Feb. 19, 2014, issued in Chinese Patent Application No. 201180047987.7, w/English translation (15 pages).
International Search Report of PCT/JP2011/072856, mailing date of Nov. 22, 2011.
Chinese Office Action dated Sep. 11, 2014, issued in counterpart Chinese Patent Application No. 201180047987.7, w/English translation (18 pages).
Notice of Grounds of Rejection dated Jun. 2, 2015, issued in corresponding Japanese Patent Application No. 2011-005033; with English translation (7 pages).
Notice of Grounds of Rejection dated Sep. 1, 2015, issued in counterpart Japanese Patent Application No. 2014-216415 (w/ English translation) (5 pages).

* cited by examiner

LIQUID MEDICATION DISPENSING MACHINE

TECHNICAL FIELD

The present invention relates to a liquid medication dispensing machine, and more particularly relates to a liquid medication dispensing machine for supplying a liquid medication from a liquid medication bottle containing the liquid medication to a prescription bottle.

BACKGROUND ART

Conventionally, a liquid medication as a liquid state medicine is dispensed in a dispensing pharmacy or the like. In accordance with a prescription for a patient, one or a plurality of types of liquid medications are infused sequentially by a predetermined quantity into a prescription bottle, and a required diluent is infused, thereby dispensing a liquid medication.

Conventional techniques related to a liquid medication dispensing machine for dispensing a liquid medication are disclosed in Japanese Laid-Open Patent Publication No. 2009-112673 (Patent Literature 1) and Japanese Laid-Open Patent Publication No. 2009-178495 (Patent Literature 2), for example. Japanese Laid-Open Patent Publication No. 2009-112673 (Patent Literature 1) proposes a liquid medication dispensing machine having a rotary unit rotated while holding a plurality of liquid medication bottles and rotating the rotary unit by 180 degrees, thereby inverting a liquid medication bottle.

Japanese Laid-Open Patent Publication No. 2009-178495 (Patent Literature 2) proposes a liquid medication dispensing machine including a pump for supplying a liquid medication from within a liquid medication bottle toward an opening of a prescription bottle via a tube, and a control device controlling driving of the pump, wherein the control device has a function of switching pump driving between a liquid medication supply state in which the liquid medication is supplied to the prescription bottle and a liquid medication stirring state in which the liquid medication in the liquid medication bottle is stirred.

CITATION LIST

Patent Literature

PTL 1: Japanese Laid-Open Patent Publication No. 2009-112673
PTL 2: Japanese Laid-Open Patent Publication No. 2009-178495

SUMMARY OF INVENTION

Technical Problem

When dispensing a liquid medication including suspensions, the prescription guidelines require that the liquid medication in a liquid medication bottle be stirred and then supplied to a prescription bottle. In the liquid medication dispensing machine described in Japanese Laid-Open Patent Publication No. 2009-112673 (Patent Literature 1), since the liquid medication contained in the liquid medication bottle is stirred by rotating the liquid medication bottle by 180 degrees to be inverted through the use of the rotary unit, the structure for stirring the liquid medication is complicated, and the liquid medication dispensing machine is increased in size.

In the case of a liquid medication dispensing machine in which a liquid medication bottle with a tube located therein is rotated, it is necessary to prevent the tube used for the liquid medication dispensing machine from rotating together with the liquid medication bottle during rotation of the liquid medication bottle so as to prevent the tube from twisting. It is disclosed that, in the liquid medication dispensing machine described in Japanese Laid-Open Patent Publication No. 2009-178495 (Patent Literature 2), the tip of one open end of a tube is inserted to reach the bottom of the liquid medication bottle. However, the subject of preventing twist of the tube and a specific structure for solving the subject are not disclosed.

The present invention was made in view of the above-described problems, and has a main object to provide a liquid medication dispensing machine capable of stirring a liquid medication contained in a liquid medication bottle in the machine with a simple structure.

Solution to Problem

A liquid medication dispensing machine according to the present invention is a liquid medication dispensing machine supplying a liquid medication from a liquid medication bottle containing the liquid medication to a prescription bottle, including a holder holding a bottom of the liquid medication bottle, and a rotationally driving unit generating rotary force and rotating the holder and the liquid medication bottle held by the holder around a rotation axis extending along a center line of the liquid medication bottle.

The liquid medication dispensing machine preferably includes a tube through which the liquid medication flowing out of the liquid medication bottle passes. The tube is located inside the liquid medication bottle and extends from the opening toward the bottom of the liquid medication bottle.

In the above-described liquid medication dispensing machine, preferably, the holder holds the liquid medication bottle with the center line displaced from the rotation axis.

In the above-described liquid medication dispensing machine, preferably, the rotationally driving unit generates the rotary force both in forward and reverse directions, and rotates the liquid medication bottle in the forward direction and then rotates the liquid medication bottle in the reverse direction opposite to the forward direction.

In the above-described liquid medication dispensing machine, preferably, the liquid medication is supplied to the prescription bottle after the rotationally driving unit rotates the liquid medication bottle.

The above-described liquid medication dispensing machine preferably includes a tube through which the liquid medication flowing out of the liquid medication bottle passes, and a positioning unit positioning the tube relative to the liquid medication bottle such that the tube passes through a central part of an opening of the liquid medication bottle. An outer diameter of the tube is formed smaller than a diameter of the opening. The tube is attached to the liquid medication bottle with the positioning unit interposed therebetween.

Here, the central part of the opening is not restricted to the central position of the opening, but indicates a region including the central position of the opening distant from the inner wall surface of the opening to such an extent that the tube arranged through the opening does not come into contact with the mouth of the liquid medication bottle.

In the above-described liquid medication dispensing machine, preferably, the positioning unit attaches the tube to the liquid medication bottle such that the tube is relatively rotated with respect to the liquid medication bottle.

In the above-described liquid medication dispensing machine, preferably, the positioning unit is attached to a main body of the liquid medication dispensing machine.

In the above-described liquid medication dispensing machine, preferably, the positioning unit is removably attached to the main body of the liquid medication dispensing machine.

In the above-described liquid medication dispensing machine, preferably, the tube includes one end located inside the liquid medication bottle and a positioning member attached to the tube at a predetermined distance from the one end. The tube is positioned relative to the liquid medication bottle by the positioning member being held by the positioning unit.

In the above-described liquid medication dispensing machine, preferably, the positioning member prevents the tube from being rotated relative to the positioning unit.

In the above-described liquid medication dispensing machine, preferably, the positioning unit holds the positioning member in a longitudinal direction of the tube.

In the above-described liquid medication dispensing machine, preferably, a base member rotating integrally with the liquid medication bottle is fixed to the opening. The positioning unit includes a cover mounted on the base member while covering the opening and not rotated while the liquid medication bottle is being rotated but sliding over the base member. The tube is engaged with the cover to be positioned relative to the liquid medication bottle.

Advantageous Effects of Invention

According to the liquid medication dispensing machine of the present invention, a liquid medication contained in a liquid medication bottle can be stirred in the machine with a simple structure.

DESCRIPTION OF EMBODIMENTS

Figure 1:
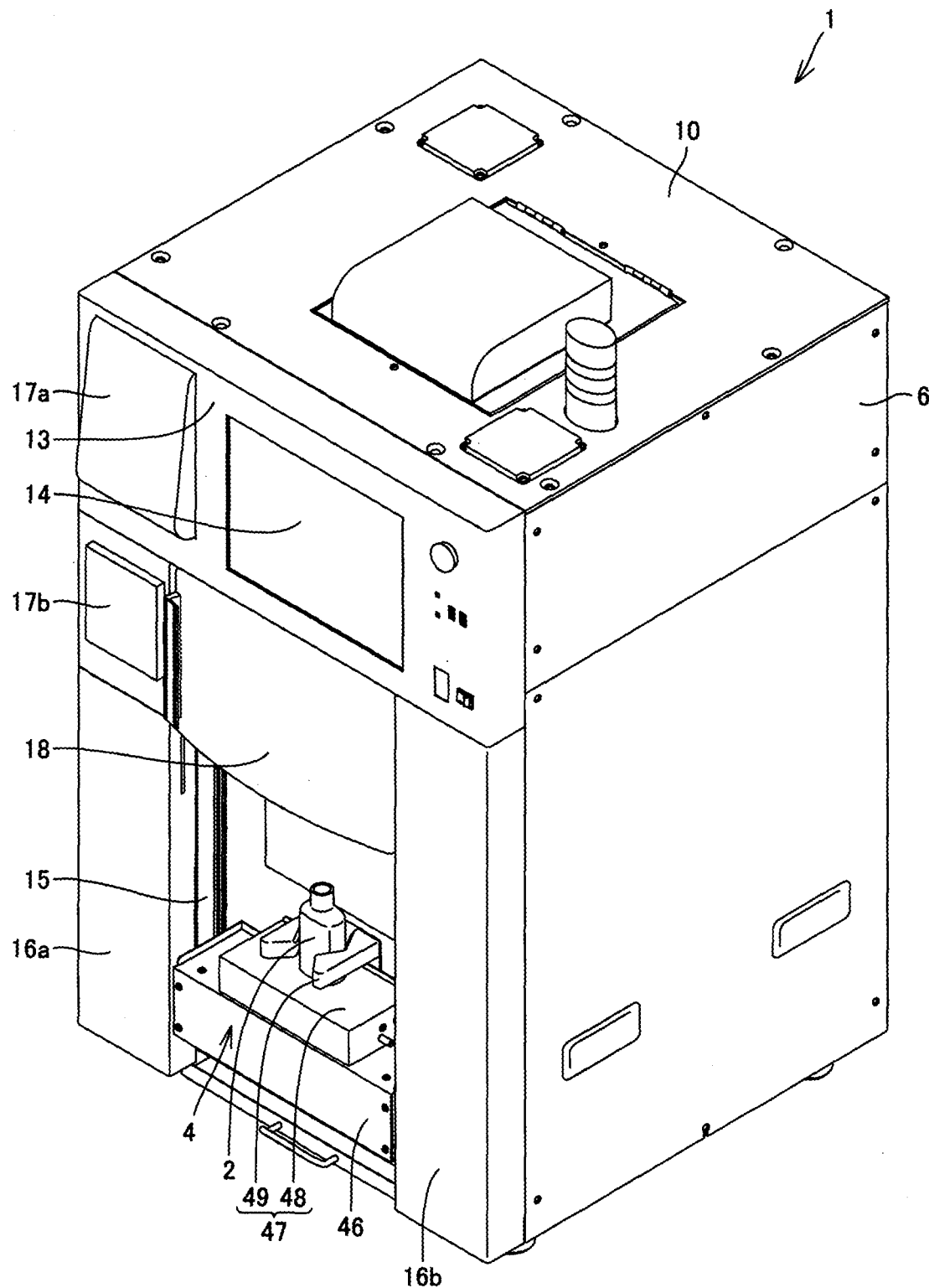
FIG. 1 is a perspective view showing a structure of a liquid medication dispensing machine of one embodiment of the present invention.

Embodiments of the present invention will be described below based on the drawings. In the following drawings, the same or corresponding portions have the same reference characters allotted, and description thereof will not be repeated.

First Embodiment

Figure 2:
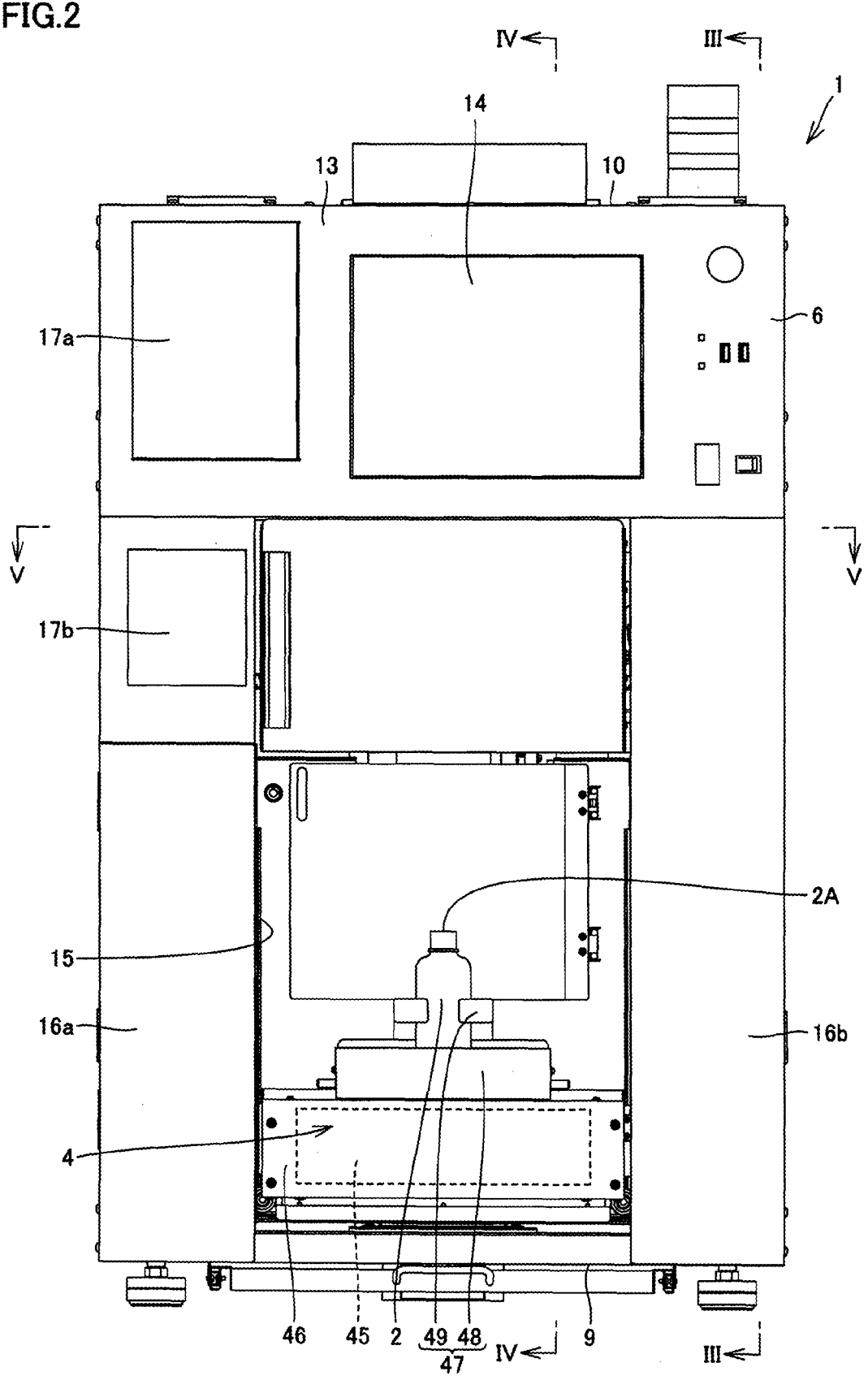
FIG. 2 is a front view of the liquid medication dispensing machine shown in FIG. 1.
Figure 3:
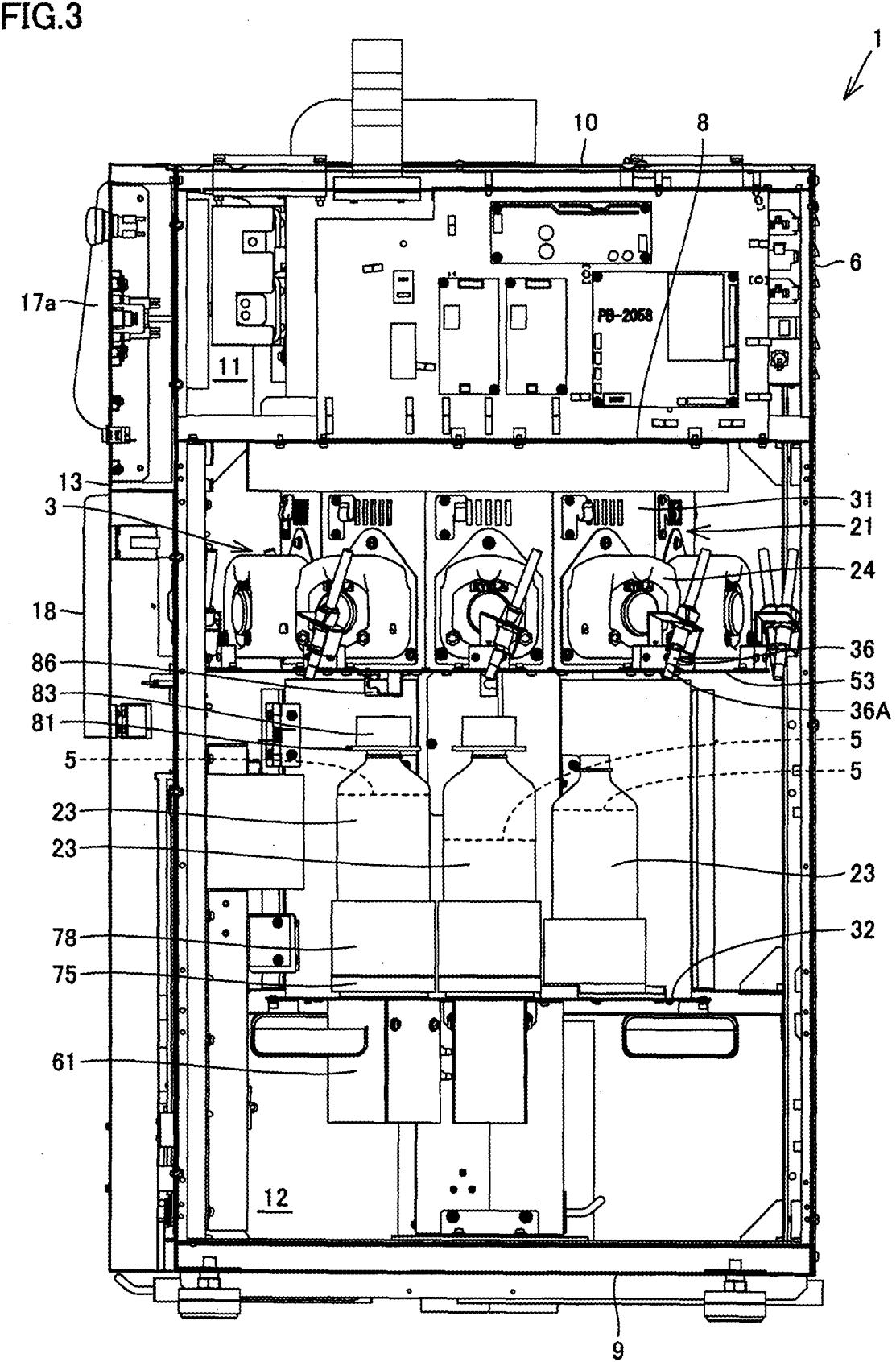
FIG. 3 is a cross sectional view of the liquid medication dispensing machine taken along the line III-III shown in FIG. 2.
Figure 4:
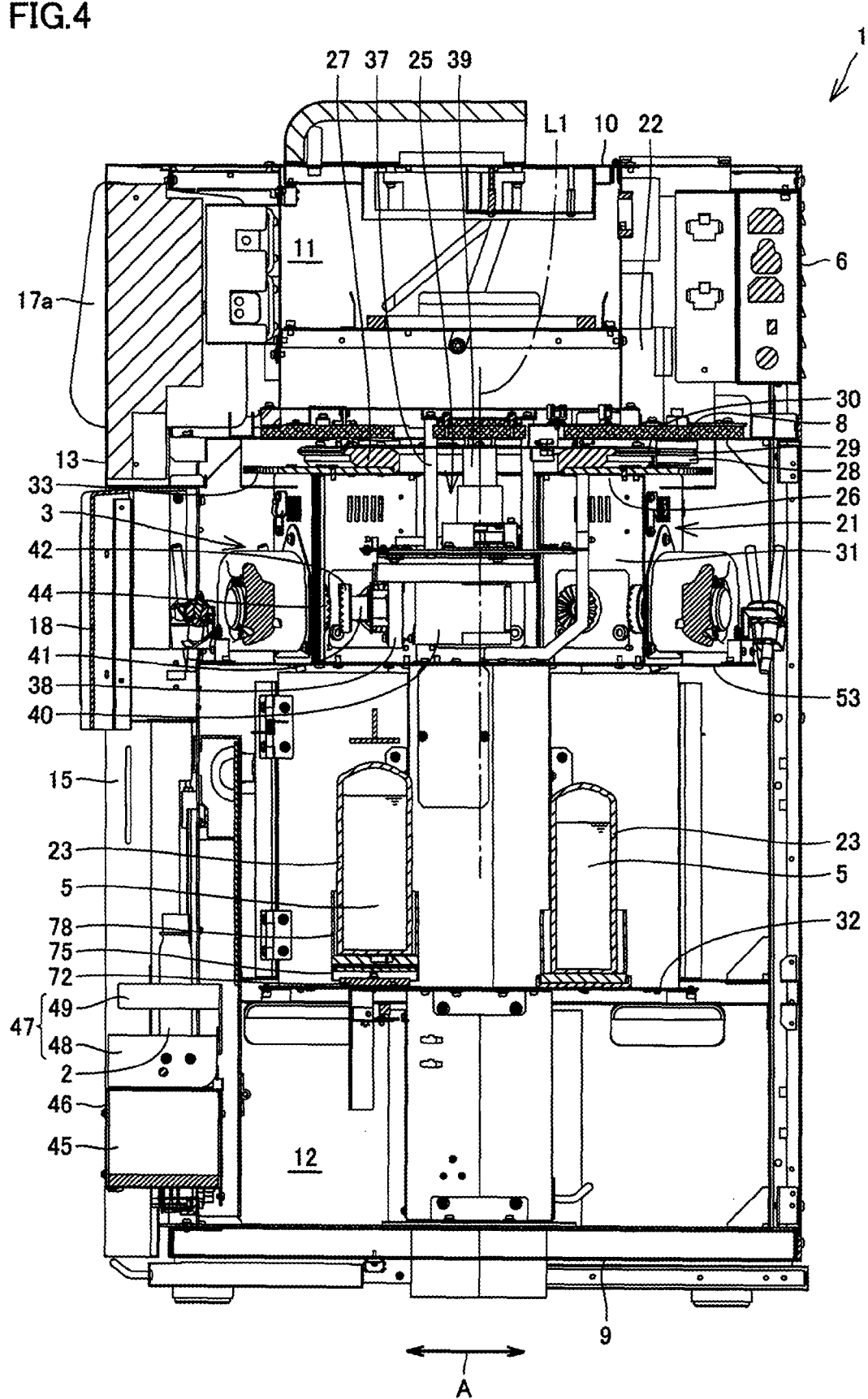
FIG. 4 is a cross sectional view of the liquid medication dispensing machine taken along the line IV-IV shown in FIG. 2.
Figure 5:
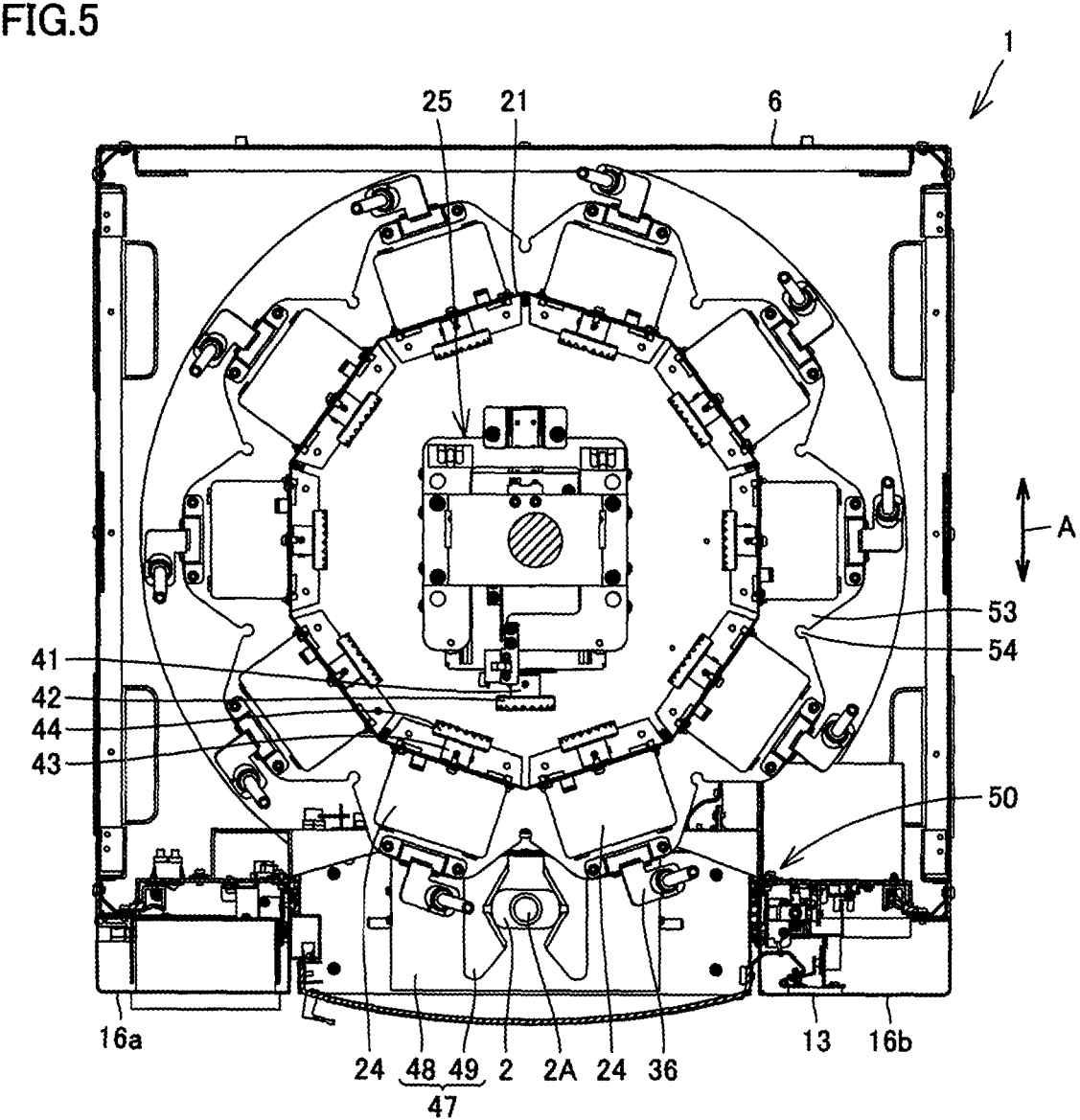
FIG. 5 is a cross sectional view of the liquid medication dispensing machine taken along the line V-V shown in FIG. 2.

FIG. 1 is a perspective view showing a structure of a liquid medication dispensing machine 1 of one embodiment of the present invention. FIG. 2 is a front view of liquid medication dispensing machine 1 shown in FIG. 1. FIG. 3 is a cross sectional view of liquid medication dispensing machine 1 taken along the line III-III shown in FIG. 2. FIG. 4 is a cross sectional view of liquid medication dispensing machine 1 taken along the line IV-IV shown in FIG. 2. FIG. 5 is a cross sectional view of liquid medication dispensing machine 1 taken along the line V-V shown in FIG. 2. Liquid medication dispensing machine 1 of the present embodiment is used to supply and dispense a liquid medication 5 which is a liquid state medicine from a liquid medication bottle 23 containing liquid medication 5 to a prescription bottle 2 in accordance with a prescription for a patient.

Liquid medication dispensing machine 1 includes a liquid medication supply unit 3 supplying liquid medication 5 from liquid medication bottle 23 to prescription bottle 2 and a weight detection unit 4 detecting the weight of liquid medication 5 contained in prescription bottle 2. The volume of liquid medication 5 supplied to prescription bottle 2 is calculated from the weight of liquid medication 5 detected by weight detection unit 4 and the specific gravity of liquid medication 5. Liquid medication supply unit 3 is controlled such that a predetermined volume of liquid medication 5 in accordance with the prescription is supplied to prescription bottle 2. Liquid medication supply unit 3 and weight detection unit 4 are provided in a housing 6. Housing 6 has a rectangular parallelepiped shape, and is installed on a horizontal installation surface in an upright position.

A support frame 8 is provided inside housing 6. Support frame 8 is located between a bottom plate 9 of housing 6 and a top plate 10 of housing 6, and in more detail, located closer to top plate 10 of housing 6. The internal space of housing 6 is divided by support frame 8 into an upper space 11 above support frame 8 and a lower space 12 below support frame 8. A touch panel 14 and printers 17a, 17b are located in a front section 13 of housing 6. A lower opening 15 by which lower space 12 communicates with the outside of housing 6 is also formed in front section 13.

Lower opening 15 is formed between both side portions 16a, 16b in front section 13 of housing 6. Above lower opening 15 between both side portions 16a, 16b, a curved plate-like front cover portion 18 is located which separates lower space 12 and the outside of housing 6. Front cover portion 18 is made of a transparent material such that lower space 12 is visible from outside the front side of housing 6. Front cover portion 18 is attached to one of both side portions 16a, 16b with a hinge and is provided to be pivotable around the axis of the hinge, so that front cover portion 18 can be opened/closed.

Liquid medication supply unit 3 has a rotation drum 21 which is a rotator located in lower space 12 and provided rotatably around an axis line (hereinbelow a "drum axis line") L1 perpendicular to support frame 8 and a drum rotating motor 22 mounted on the upper surface of support frame 8 and rotating rotation drum 21 around drum axis line L1 relative to support frame 8. Liquid medication supply unit 3 also has a plurality of pumps 24 provided for rotation drum 21 and transporting a liquid medication from a plurality of liquid medication bottles 23 containing liquid medication 5 to prescription bottle 2, and a pump driving unit 25 driving each pump 24. Each pump 24 may be a tube pump.

Rotation drum 21 has a pump holder 31 holding each pump 24 and a liquid medication bottle holder 32 holding each liquid medication bottle 23 in an upright position such that an opening 23A (see FIG. 10 which will be described later) is open upward. Liquid medication bottle holder 32 is provided below pump holder 31 and has an annular flat plate shape in plan view. On pump holder 31, respective pumps 24 are located at intervals in a circumferential direction around drum axis line L1 (hereinbelow a "drum circumferential direction"). On liquid medication bottle holder 32, respective liquid medication bottles 23 are located at intervals in the drum circumferential direction.

The number of liquid medication bottles 23 and pumps 24 mounted on rotation drum 21 in the present embodiment can be optionally changed according to the purpose. A different liquid medication 5 may be contained in each of plurality of liquid medication bottles 23, or heavily used liquid medication 5 of the same type may be contained in plurality of liquid medication bottles 23, or a diluent, such as water or simple syrup, may be contained in one or a plurality of liquid medication bottles 23.

Pump driving unit 25 for selectively driving each pump 24 has a fixed part 37 fixed to support frame 8, a moving part 38 provided movably forward and backward relative to fixed part 37 (in the direction of a double-headed arrow A shown in FIGS. 4 and 5), a moving motor 39 which is fixed to fixed part 37 and moves moving part 38 forward and backward relative to fixed part 37, and a pump driving motor 40 which is fixed to moving part 38 and drives pump 24. Pump driving motor 40 may be implemented by a stepping motor.

A coupling member 42 is fixed at the leading end of drive shaft 41 rotated by pump driving motor 40. A coupled member 44 to be coupled to coupling member 42 is fixed to a rotary shaft 43 of the rotor of each pump 24. When coupling member 42 and coupled member 44 are coupled to each other, rotation of pump driving motor 40 is transmitted to pump 24. Each pump 24 is constructed to be driven individually in conjunction with intermittent driving of drum rotating motor 22. The speed of supply of liquid medication 5 to prescription bottle 2 increases as the speed of rotation of pump driving motor 40 increases.

By driving moving motor 39, pump driving motor 40 is moved forward and backward. By this movement of pump driving motor 40, a switch can be made between a coupled state in which coupling member 42 of pump driving motor 40 is coupled to coupled member 44 of pump 24 and a decoupled state in which coupling member 42 is not coupled to coupled member 44.

For example, coupling member 42 and coupled member 44 can be coupled to each other by advancing moving part 38 by driving of moving motor 39. The coupling of coupling member 42 and coupled member 44 can be released by retracting moving part 38 by driving of moving motor 39. Rotation drum 21 can be rotated relative to support frame 8 in the decoupled state.

By driving drum rotating motor 22 in the decoupled state, rotation drum 21 is rotated to a position where coupled member 44 of a specific pump 24 selected based on prescription information input to liquid medication dispensing machine 1 faces coupling member 42 of pump driving motor 40, and after the rotation, a switch is made to the coupled state. The selected specific pump 24 can thereby be driven to dispense liquid medication 5 supplied from a desired liquid medication bottle 23 into prescription bottle 2. Although coupling member 42 and coupled member 44 are both implemented by gears, they may have any structure that can transmit motive power.

At an upper end 26 of rotation drum 21, a ring member 27 located horizontally and coaxially with drum axis line L1 is located rotatably around drum axis line L1. Three or more support members 28 supporting ring member 27 are provided on the outer circumferential side of ring member 27. Respective support members 28 are located at equal intervals in the drum circumferential direction.

Respective support members 28 are provided relatively rotatably with respect to support frame 8 around an axis line parallel to drum axis line L1. A recessed groove 29 is formed in the flat cylindrical outer circumferential surface of each of support members 28 along the entire circumference. An annular protruding line 30 is formed in the outer circumferential part of ring member 27 along the entire circumference. Protruding line 30 of ring member 27 is fitted into recessed groove 29 of each support member 28. Ring member 27 and support member 28 are provided relatively rotatably.

Drum rotating motor 22 is fixed to support frame 8. A driving gear (not shown) is fixed to the rotary shaft of drum rotating motor 22. A driven gear 33 meshing with the driving gear is fixed to upper end 26 of rotation drum 21. Driven gear 33 has an annular thin plate shape and is fixed to the lower surface of ring member 27. Rotation of drum rotating motor 22 is transmitted to ring member 27 via the driving gear and driven gear 33, and ring member 27 and rotation drum 21 to which the ring member is fixed are thereby rotated integrally. With such a structure, rotation drum 21 can be smoothly rotated relative to support frame 8.

Drum rotating motor 22 revolves integrally in the horizontal direction plurality of liquid medication bottles 23 mounted on rotation drum 21, pumps 24 and supply nozzles 36 provided in correspondence with plurality of liquid medication bottles 23, respectively, and a tube 34, which will be described later, with one end located inside liquid medication bottle 23 and the other end attached to supply nozzle 36.

Supply nozzle 36 is attached onto the same circumference as the outer circumferential part of a nozzle attachment plate 53 which is an annular flat plate provided at the lower end of pump holder 31. Respective supply nozzles 36 are located on nozzle attachment plate 53 at equal intervals in the drum circumferential direction on a virtual circle around drum axis line L1. Supply nozzle 36 is attached to nozzle attachment plate 53 at an inclination of a predetermined angle with respect to drum axis line L1. Nozzle attachment plate 53 is located above liquid medication bottle holder 32. Nozzle attachment plate 53 and liquid medication bottle holder 32 are parallel to each other, and are constructed to be capable of revolving on a horizontal plane together with rotation drum 21 around drum axis line L1.

Weight detection unit 4 is located in lower opening 15. Weight detection unit 4 has an electronic balance 45, a casing 46 storing electronic balance 45, and a prescription bottle holder 47 mounted on and fixed to electronic balance 45 and holding prescription bottle 2 in an upright position such that an opening 2A is open upward. Electronic balance 45 detects the weight of liquid medication 5 supplied to prescription bottle 2. When the weight of liquid medication 5 reaches a predetermined value, liquid medication supply unit 3 stops driving of pump 24 to stop supply of liquid medication 5 to prescription bottle 2. Electronic balance 45 may be of any type, such as tuning fork, load cell or electromagnetic type. Casing 46 is provided at a lower position of front section 13 of housing 6 between both side portions 16a, 16b. Prescription bottle holder 47 has a table 48 on which prescription bottle 2 is mounted and a holding fixture 49 provided above table 48 and holding prescription bottle 2.

Weight detection unit 4 is moved up and down by an elevating device 50 as a driving unit shown in FIG. 5. Elevating device 50 moves weight detection unit 4 in the vertical direction so as to be located at two positions, an initial position and a supply position, and accordingly moves prescription bottle 2 mounted on table 48 of weight detection unit 4. The initial position is a position where prescription bottle 2 is placed on table 48 of liquid medication dispensing machine 1. The supply position is a position where prescription bottle 2 and supply nozzle 36 come closer to each other than at the initial position so that liquid medication 5 is supplied to prescription bottle 2. By means of elevating device 50, prescription bottle 2 is reciprocally moved between the outside and the inside of housing 6 of liquid medication dispensing machine 1 so as to reciprocate between the initial position and the supply position.

Figure 6:
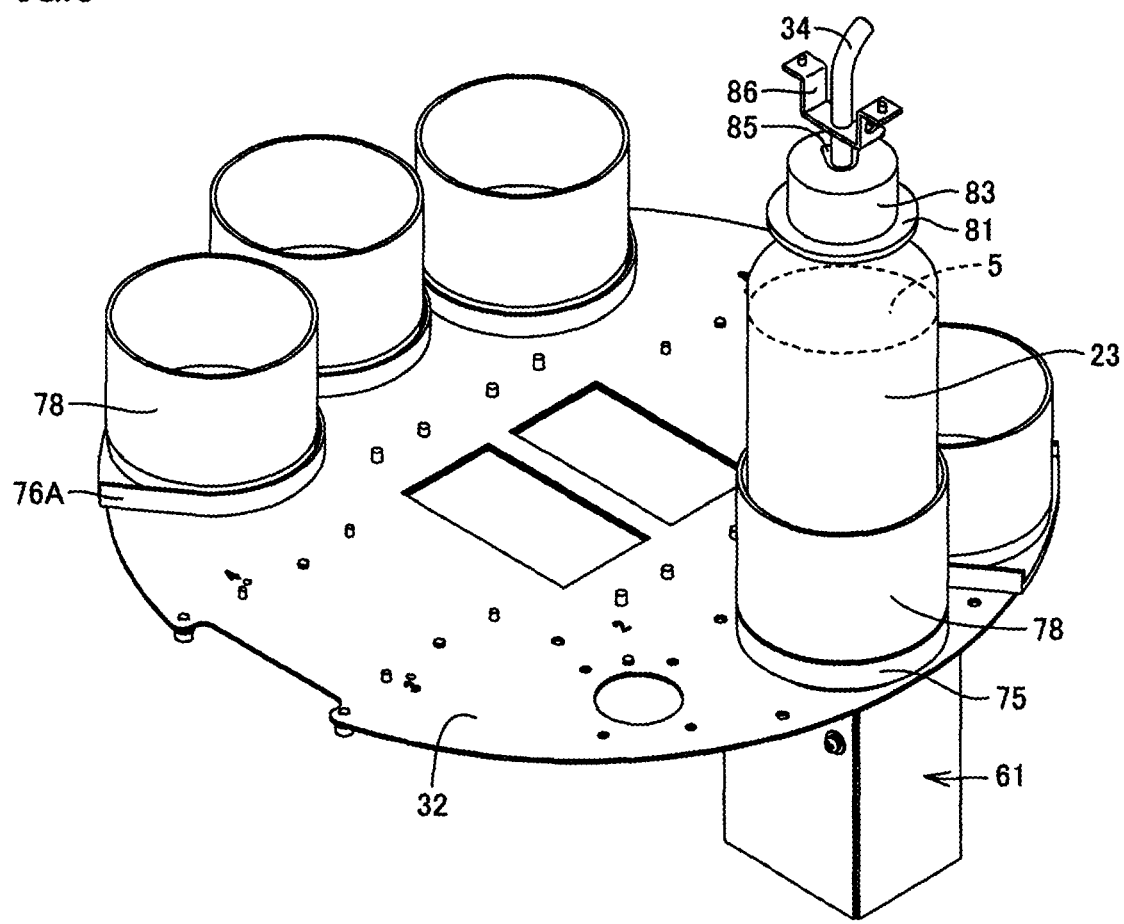
FIG. 6 is a perspective view showing a structure of a stirring unit by which a liquid medication in a liquid medication bottle is stirred.
Figure 7:
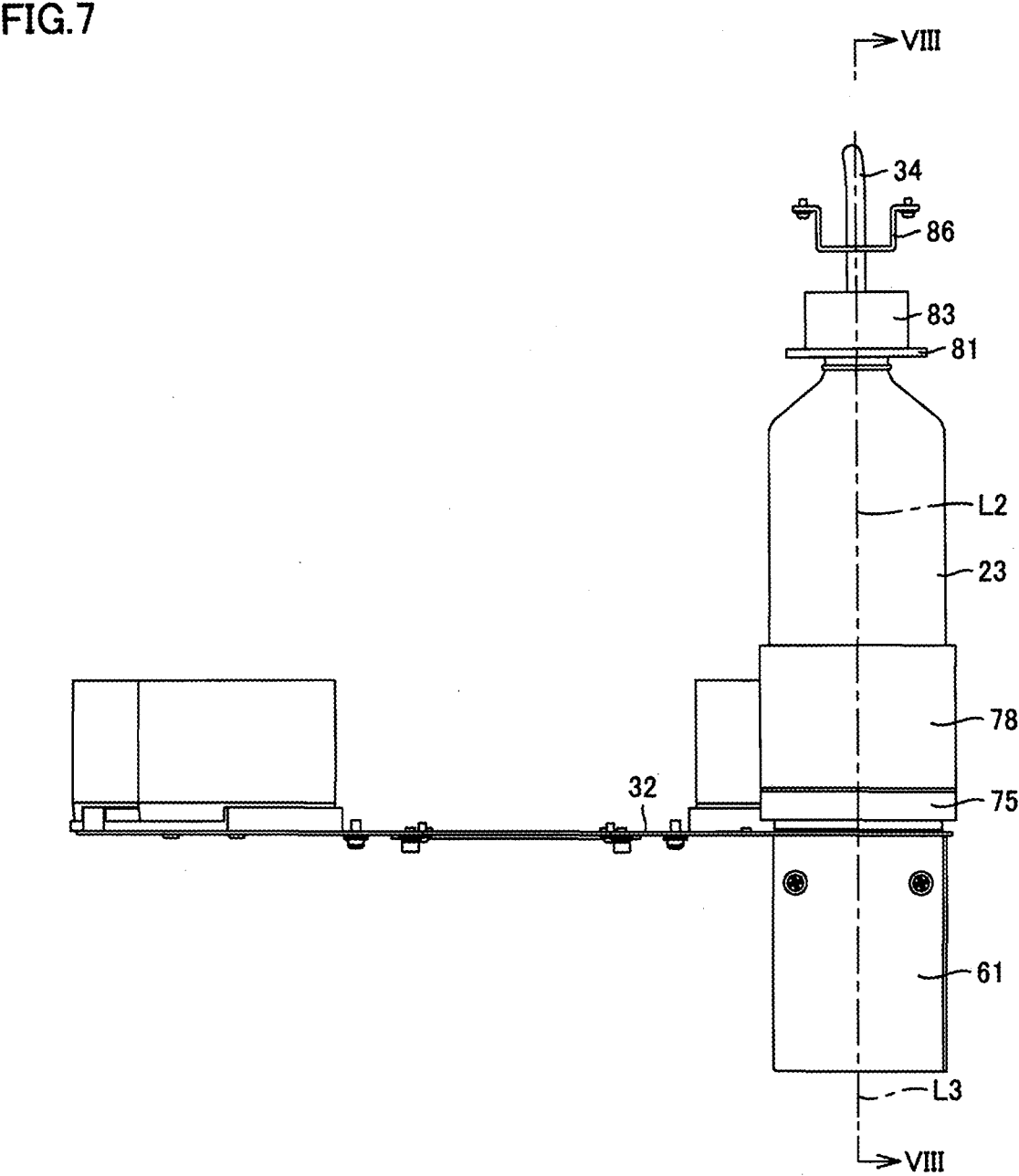
FIG. 7 is a side view of the stirring unit shown in FIG. 6.
Figure 8:
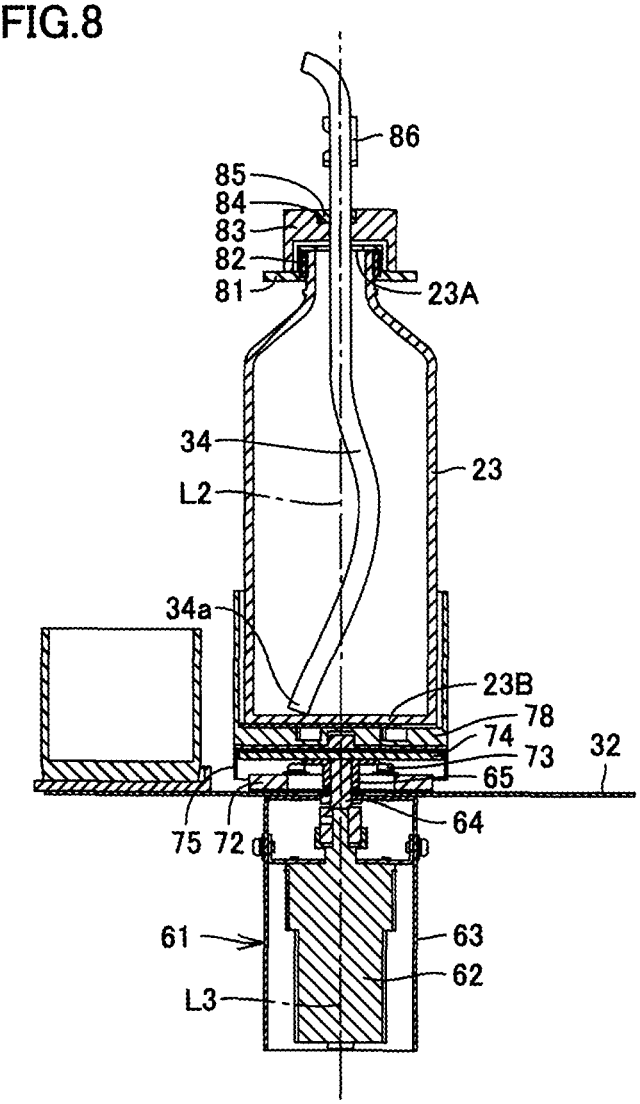
FIG. 8 is a cross sectional view of the stirring unit taken along the line VIII-VIII shown in FIG. 7.
Figure 9:
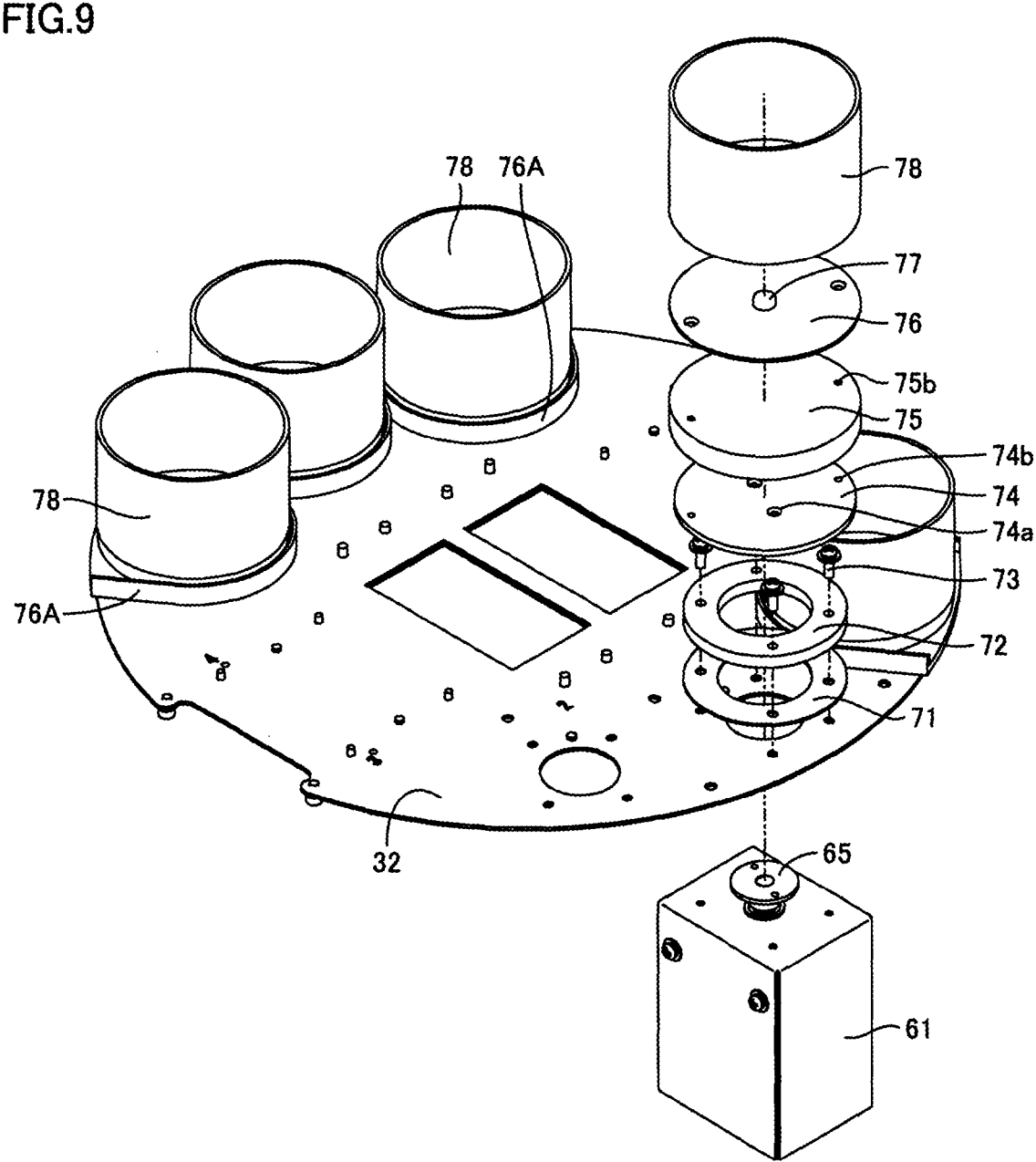
FIG. 9 is an exploded perspective view of the stirring unit.

FIG. 6 is a perspective view showing a structure of a stirring unit by which liquid medication 5 in liquid medication bottle 23 is stirred. FIG. 7 is a side view of the stirring unit shown in FIG. 6. FIG. 8 is a cross sectional view of the stirring unit taken along the line VIII-VIII shown in FIG. 7. FIG. 9 is an exploded perspective view of the stirring unit. Liquid medication supply unit 3 of the present embodiment includes, in housing 6 of liquid medication dispensing machine 1, a stirring device stirring liquid medication 5 contained in liquid medication bottle 23. This stirring device will be described in detail below.

In FIGS. 6 to 9 and FIG. 10 which will be described later, liquid medication bottle holder 32 with merely one liquid medication bottle 23 mounted thereon is shown giving priority to clarity. Although liquid medication dispensing machine 1 includes a plurality of cup fixing parts 76, 76A, cups 78 and the like for holding liquid medication bottles 23, merely some of plurality of cup fixing parts 76, 76A, cups 78 and the like are illustrated in FIGS. 6 to 10, and not all of them are illustrated.

A rotationally driving unit 61 generating rotary force is located under liquid medication bottle holder 32. As shown in FIG. 8, rotationally driving unit 61 has a motor 62 as an example of a power source and a box 63 storing motor 62 therein. A shaft 64 rotating with motor 62 is coupled to the rotary shaft of motor 62. Shaft 64 is fixed to motor 62 rotatably around a rotation axis L3 integrally with motor 62. Shaft 64 is located to extend from the inside to the outside of box 63. Shaft 64 is located to extend through flat plate-like liquid medication bottle holder 32 in the vertical direction, and transmits rotary force generated by motor 62 from the lower side of liquid medication bottle holder 32 to the upper side of liquid medication bottle holder 32.

Cup 78 is fixed to shaft 64 with various elements, which will be described later, interposed therebetween. Cup 78 serves as a holder holding liquid medication bottle 23. Cup 78 holds the bottom 23B side of liquid medication bottle 23 shown in FIG. 8. Cup 78 has a bottomed hollow cylindrical shape. Liquid medication bottle 23 is received in cup 78 such that bottom 23B is opposed to the inner bottom surface of cup 78. The inner wall surface of the sidewall of cup 78 has a diameter slightly larger than that of the side surface of liquid medication bottle 23. Therefore, the side surface of liquid medication bottle 23 is opposed to the inner wall surface of the sidewall of cup 78 with a minute clearance. Part of the side surface of liquid medication bottle 23 may contact the inner wall surface of the sidewall of cup 78.

Tube 34 as a pipe part is located inside liquid medication bottle 23. Tube 34 is provided for each of plurality of liquid medication bottles 23. Tube 34 is made of a material having flexibility and elasticity, and is deformable in cross section under pressure and is elastically restored by releasing pressure. Tube 34 may be made of synthetic resin, such as a silicon tube, for example. Tube 34 extends from opening 23A toward bottom 23B of liquid medication bottle 23, and is located inside liquid medication bottle 23 such that its one end 34a contacts the inner surface of bottom 23B of liquid medication bottle 23.

Figure 10:
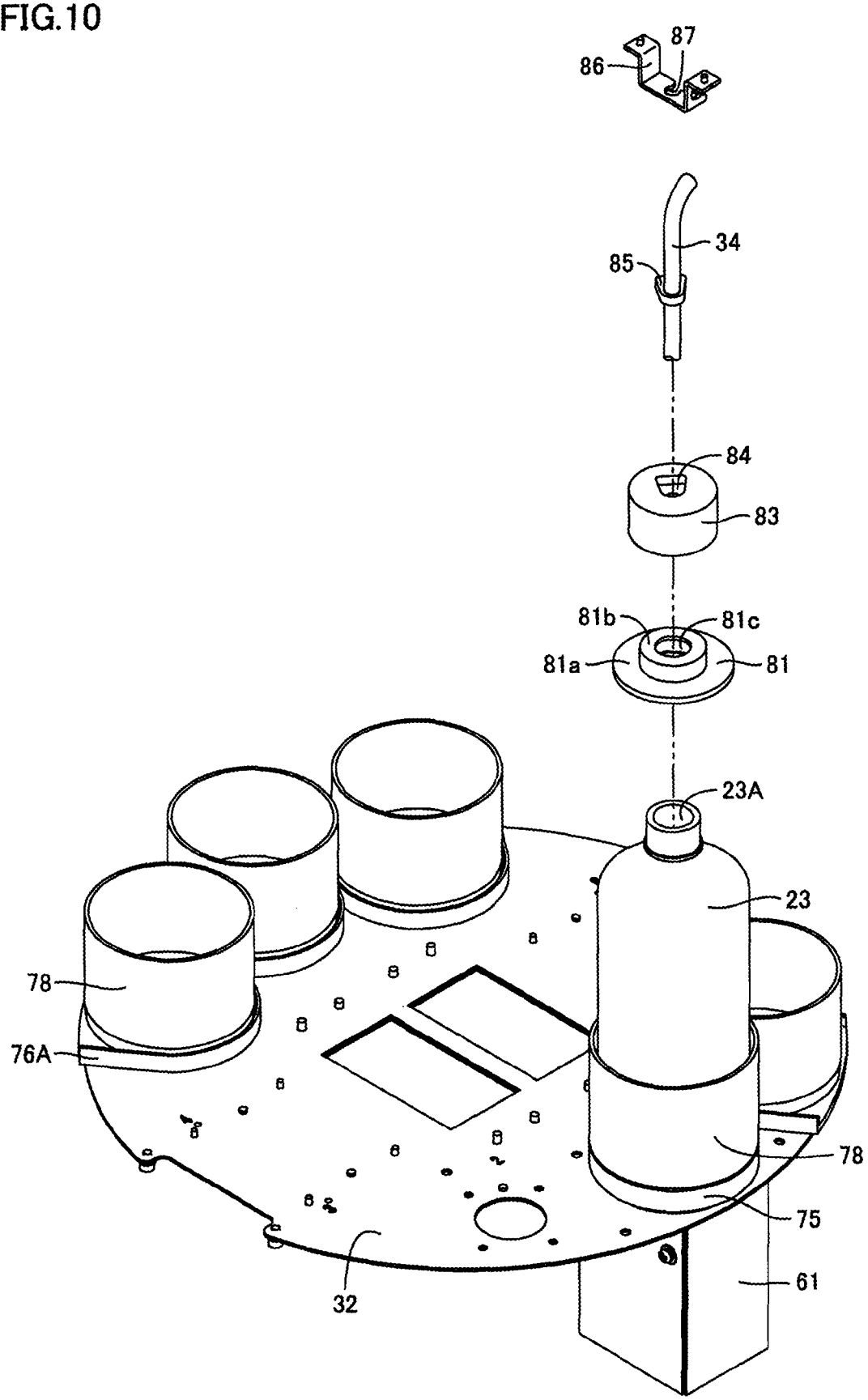
FIG. 10 is an exploded perspective view of an attachment structure by which a tube is attached to the liquid medication bottle.

FIG. 10 is an exploded perspective view of an attachment structure by which a tube is attached to liquid medication bottle 23. Referring to FIGS. 7, 8 and 10, a base member 81 is fixed to opening 23A of liquid medication bottle 23. Base member 81 has an annular disc-like flange portion 81a and a cylindrical sleeve portion 81b projecting from the upper surface of flange portion 81a. A through-hole 81c extending through the disc member is formed at the central part of the disc member that forms an end of sleeve portion 81b. The inside and the outside of liquid medication bottle 23 communicate with each other via through-hole 81c with base member 81 attached to opening 23A of liquid medication bottle 23. Tube 34 is inserted into through-hole 81c to extend through through-hole 81c, and is located to extend from the outside to the inside of liquid medication bottle 23.

Base member 81 is fixed to opening 23A of liquid medication bottle 23 as shown in FIG. 8. A cylindrical spacer 82 made of an elastic material, such as silicone rubber, for example, is attached to the inner circumferential surface of sleeve portion 81b of base member 81. Base member 81 is attached to liquid medication bottle 23 with elastically deformable spacer 82 interposed therebetween such that base member 81 can be reliably fixed to opening 23A of liquid medication bottle 23 even if dimensional variations in base member 81 or liquid medication bottle 23 occur.

A cover 83 is located over base member 81. Cover 83 is mounted on the upper surface of flange portion 81a of base member 81 while not being fixed to base member 81. Cover 83 has a cap shape having a hollow cylindrical wall portion and a disk-like top portion covering the upper end of the wall portion. The lower end of the wall portion comes into contact with the upper surface of base member 81, so that cover 83 is mounted over base member 81. Cover 83 is provided to cover opening 23A of liquid medication bottle 23 while cover 83 is mounted on base member 81 fixed to liquid medication bottle 23. A through-hole having a diameter of such a degree that tube 34 can be just inserted therethrough is formed in the above-mentioned top portion of cover 83.

The above-mentioned top portion of cover 83 further has a recess 84 obtained by recessing part of the upper surface. A positioning member 85 is attached to tube 34. Positioning member 85 is attached to tube 34 so as not to block the flow of liquid medication 5 flowing through the inside of tube 34. Moreover, positioning member 85 is attached to tube 34 so as to be unlikely to move relative to tube 34 in the longitudinal direction of tube 34. Recess 84 and positioning member 85 have a corresponding shape such that positioning member 85 is fitted within recess 84.

Positioning member 85 is engaged with recess 84 formed in cover 83 to thereby position tube 34 with positioning member 85 attached thereto relative to liquid medication bottle 23. As shown in FIG. 8, when positioning member 85 is received in recess 84 of cover 83, positioning member 85 positions tube 34 relative to liquid medication bottle 23 such that one end 34a of tube 34 slightly curved inside liquid medication bottle 23 contacts bottom 23B of liquid medication bottle 23.

Furthermore, a tube fixing part 86 for fixing tube 34 on the outside of liquid medication bottle 23 is provided. Tube fixing part 86 is fixed to the lower surface side of nozzle attachment plate 53 as shown in FIG. 3. Tube fixing part 86 has a cutout 87 formed therein. Cutout 87 has a shape nearly identical to the outer diameter of tube 34 such that tube 34 can be held within cutout 87. By causing tube 34 to be held within cutout 87 with tube 34 inserted into liquid medication bottle 23 as illustrated in FIGS. 7 and 8, tube 34 is fixed to nozzle attachment plate 53. Furthermore, tube 34 is fitted within a cutout 54 (see FIG. 5) formed in nozzle attachment plate 53, and is thereby fixed to nozzle attachment plate 53.

Figure 11:
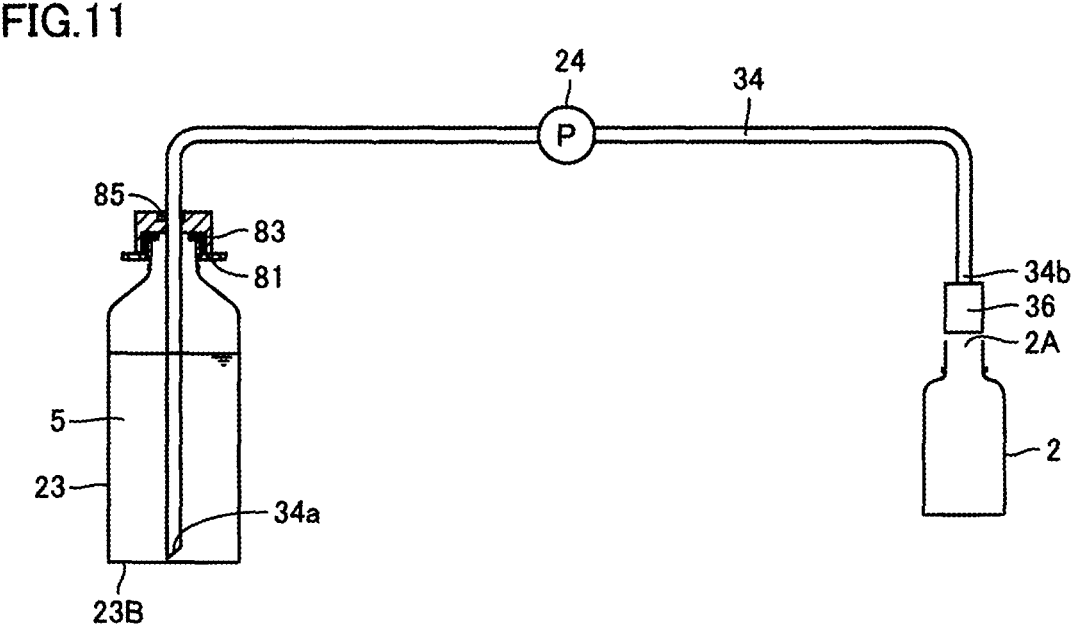
FIG. 11 is a schematic diagram showing the overall structure of the tube.

FIG. 11 is a schematic diagram showing the overall structure of tube 34. As described above, open one end 34a of tube 34 is inserted to reach bottom 23B of liquid medication bottle 23, and is immersed into liquid medication 5 in liquid medication bottle 23. The other end 34b of tube 34 which is an end opposite to one end 34a is attached to supply nozzle 36. If pump 24 described above is a tube pump, a middle portion of tube 34 between one end 34a and the above-mentioned other end is inserted into pump 24 and is removably held by pump 24.

Pump 24 is used as a power source by which liquid medication 5 in liquid medication bottle 23 is sucked toward supply nozzle 36. When supplying liquid medication 5 from liquid medication bottle 23 to prescription bottle 2 by driving of pump 24, liquid medication 5 flown out of liquid medication bottle 23 flows from one end 34a, through the inside of tube 34, via a supply port 36A which is an open end of supply nozzle 36, and into prescription bottle 2.

Positioning member 85 described above is attached to tube 34 at a predetermined distance from one end 34a of tube 34. Positioning member 85 is attached to tube 34 such that the distance from one end 34a of tube 34 to the position of tube 34 where positioning member 85 is attached is kept constant. Tube 34 with positioning member 85 attached thereto can thus be prepared, and tube 34 can be reliably positioned relative to liquid medication bottle 23 in an easy operation of fitting positioning member 85 into recess 84 formed in cover 83. The position of positioning member 85 in the longitudinal direction of tube 34 is set such that one end 34a of tube 34 is reliably immersed in liquid medication 5 in liquid medication bottle 23, typically, to such a degree that one end 34a contacts bottom 23B of liquid medication bottle 23.

In the stirring device having the structure described above, when motor 62 of rotationally driving unit 61 is driven, shaft 64 fixed to motor 62 is rotated together with motor 62. The direction of rotation of motor 62 at this time will be called a forward direction. Cup 78 fixed to shaft 64 and liquid medication bottle 23 held by cup 78 are rotated around rotation axis L3 along with the rotation of shaft 64 in the forward direction. Rotation axis L3 forming the central axis of rotation of liquid medication bottle 23 extends along a center line L2 of liquid medication bottle 23. Here, center line L2 of liquid medication bottle 23 refers to a straight line connecting opening 23A and bottom 23B of liquid medication bottle 23, and typically refers to a straight line connecting the center of opening 23A of liquid medication bottle 23 of circular shape in plan view and the center of bottom 23B of liquid medication bottle 23 of circular shape in plan view.

In the embodiment illustrated in FIGS. 7 and 8, liquid medication bottle 23 is located at the center of cup 78. Center line L2 of liquid medication bottle 23 and rotation axis L3 of rotationally driving unit 61 thus reside on the same straight line.

Along with the rotation of this liquid medication bottle 23, liquid medication 5 contained in liquid medication bottle 23 flows inside liquid medication bottle 23 in the circumferential direction of the cylindrical side portion of liquid medication bottle 23 in the direction of rotation of liquid medication bottle 23.

After motor 62 is rotated for a predetermined time in the forward direction, motor 62 is subsequently rotated in the reverse direction opposite to the forward direction. Rotationally driving unit 61 is provided so as to be capable of generating rotary force both in the forward and reverse directions. Liquid medication dispensing machine 1 may be constructed to allow an operator who operates liquid medication dispensing machine 1 to optionally set the direction of rotation and time of rotation of motor 62. For example, the time of rotation of motor 62 in the forward direction and the time of rotation in the reverse direction may be made equal, such as by rotating motor 62 in the forward direction for 5 seconds to rotate liquid medication bottle 23 several times, and then rotating motor 62 in the reverse direction for 5 seconds to rotate liquid medication bottle 23 several times in the reverse direction. Alternatively, for example, the direction of rotation of motor 62 may be set to be the forward direction alone.

Along with the change of the direction of rotation of motor 62, the direction of rotation of liquid medication bottle 23 is also changed. That is, rotationally driving unit 61 rotates liquid medication bottle 23 in the forward direction, and then rotates liquid medication bottle 23 in the reverse direction opposite to the forward direction. Inside liquid medication bottle 23 having been changed in the direction of rotation and being rotated in the reverse direction, the turbulence intensity of a turbulent flow in the flow of liquid medication 5 increases. In addition, a vortex occurs in the flow of liquid medication 5. Liquid medication 5 is stirred inside liquid medication bottle 23 by the action of this turbulent flow and vortex.

In this way, liquid medication 5 contained in liquid medication bottle 23 can be stirred inside liquid medication dispensing machine 1 by rotating liquid medication bottle 23 by the rotation driving power generated by rotationally driving unit 61. Therefore, liquid medication 5 which needs stirring can be dispensed efficiently in a short time through the use of liquid medication dispensing machine 1 of the present embodiment. With a simple structure obtained by adding rotationally driving unit 61 to a conventional device, cup 78 holding liquid medication bottle 23 and liquid medication bottle 23 can be rotated integrally to stir liquid medication 5 inside liquid medication dispensing machine 1. Since the turbulence intensity of the turbulent flow in liquid medication bottle 23 can be increased by switching the direction of rotation of liquid medication bottle 23 from the forward direction to the reverse direction, liquid medication 5 can be stirred more efficiently.

Tube 34 is located inside liquid medication bottle 23 to extend from opening 23A to bottom 23B of liquid medication bottle 23, and tube 34 is fixed on the outside of liquid medication bottle 23. Therefore, tube 34 is relatively rotated with respect to liquid medication bottle 23 being rotated. Since tube 34 is kept fixed relative to liquid medication 5 flowing through the inside of liquid medication bottle 23 together with liquid medication bottle 23, tube 34 serves as a stirrer for liquid medication 5. That is, by locating tube 34 inside liquid medication bottle 23 to be immersed in liquid medication 5, the flow of liquid medication 5 is more likely to become a turbulent flow. Liquid medication 5 can therefore be stirred more efficiently.

When tube 34 located inside liquid medication bottle 23 is rotated together with liquid medication bottle 23, tube 34 may be twisted. If tube 34 is twisted, a problem, such as removal of tube 34 from liquid medication bottle 23, falling of liquid medication bottle 23 or damage to tube 34, may occur. Therefore, the present embodiment presents a structure where, when rotationally driving unit 61 rotates liquid medication bottle 23, base member 81 fixed to opening 23A of liquid medication bottle 23 is rotated integrally with liquid medication bottle 23, but cover 83 mounted on base member 81 slides over base member 81 without rotation. Tube 34 is fixed to nozzle attachment plate 53, and is attached to cover 83 capable of relatively rotating with respect to base member 81.

The diameter of opening 23A of liquid medication bottle 23 and the diameter of through-hole 81c formed in base member 81 are formed somewhat larger than the outer diameter of tube 34. By aligning the position of the through-hole formed in cover 83 through which tube 34 can be inserted with opening 23A of liquid medication bottle 23 and through-hole 81c formed in base member 81, tube 34 is positioned relative to liquid medication bottle 23 so as to pass through the central part of opening 23A and through-hole 81c as shown in FIG. 8. Base member 81, cover 83 and positioning member 85 constitute a positioning unit that positions tube 34 relative to liquid medication bottle 23 so as to pass through the central part of opening 23A. Tube 34 is attached to liquid medication bottle 23 with this positioning unit interposed therebetween.

Since such a structure can prevent tube 34 from contacting opening 23A, tube 34 can be prevented from being rotated together with liquid medication bottle 23 while liquid medication bottle 23 is being rotated. Therefore, the occurrence of twist of tube 34 can be prevented, and the occurrence of a problem that would be caused by twist of tube 34 as described above can be prevented. It is also possible to prevent tube 34 from contacting liquid medication bottle 23 and base member 81 being rotated and to prevent the outer surface of tube 34 from being worn out. Therefore, damage to tube 34 can be prevented, and wear debris of tube 34 can be prevented from entering liquid medication bottle 23.

By fitting positioning member 85 into recess 84 of cover 83 so that positioning member 85 is held by cover 83, tube 34 is engaged with cover 83, and tube 34 can be easily positioned relative to liquid medication bottle 23 so as to pass through the central part of opening 23A, which can easily prevent the occurrence of twist or wear of tube 34.

As shown in FIG. 10, recess 84 formed in cover 83 has the form extending in the direction from the central part of cover 83 to the radially outer side, and positioning member 85 to be attached to tube 34 has the form corresponding to recess 84. That is, positioning member 85 extends in the direction crossing (typically, orthogonal to) the direction in which tube 34 extends. Tube 34 extends through positioning member 85 on the one end side of positioning member 85 in the direction in which positioning member 85 extends, and the other end side opposite to the above-mentioned one end side protrudes from the surface of tube 34 so as to project from tube 34 to the radially outside of tube 34. By thus forming positioning member 85, positioning member 85 has a rotation stopping function to prevent tube 34 from rotating relative to cover 83. Therefore, wear of tube 34 and cover 83 can be prevented, and wear of positioning member 85 and cover 83 can be prevented.

At the time of rotation of liquid medication bottle 23, base member 81 is rotated together with liquid medication bottle 23 while being in contact with cover 83 not being rotated. Therefore, at the contact sliding portion between base member 81 and cover 83, the material forming base member 81 or cover 83 is worn out. However, base member 81 has flat plate-like flange portion 81a and sleeve portion 81b projecting from flange portion 81a, and cover 83 is mounted on flange portion 81a, and through-hole 81c for locating tube 34 to extend through cover 83 is formed at the upper end of sleeve portion 81b. Therefore, wear debris of base member 81 and cover 83 can be prevented from entering liquid medication bottle 23 via through-hole 81c.

In the stirring device of the present embodiment, rotationally driving unit 61 is located under liquid medication bottle 23, and shaft 64 that transmits rotary force extends through box 63 and liquid medication bottle holder 32 to project upward from rotationally driving unit 61. If liquid medication 5 enters motor 62 along shaft 64, a problem may occur in motor 62. Therefore, a waterproof structure for preventing liquid medication 5 from entering motor 62 in case that liquid medication 5 spills during handling of liquid medication bottle 23 to thereby protect motor 62 is provided on the upper surface of liquid medication bottle holder 32. This waterproof structure will be described below.

As shown in FIGS. 8 and 9, the end of shaft 64 coupled to motor 62 is covered by a cap-like coupling shaft 65. Shaft 64 is located to extend through the through-hole formed in liquid medication bottle holder 32 to span the upper and lower sides of liquid medication bottle holder 32. Coupling shaft 65 is located on the upper side of liquid medication bottle holder 32. Coupling shaft 65 is attached to shaft 64 removably in consideration of ease of maintenance.

An annular sheet member 71 made of an elastic material is located in contact with the upper surface of liquid medication bottle holder 32 so as to surround the through-hole formed in liquid medication bottle holder 32 for shaft 64 to extend therethrough. Sheet member 71 is held between liquid medication bottle holder 32 and an annular pressing member 72. Pressing member 72 is fixed to liquid medication bottle holder 32 by a fixing member 73 represented by a plurality of bolts. Pressing member 72 is fixed to liquid medication bottle holder 32 while applying stress on sheet member 71 in the thickness direction and keeping sheet member 71 in an elastically deformed state in its entirety in the circumferential direction. Accordingly, the circumference of the through-hole formed in liquid medication bottle holder 32 is sealed liquid tightly, which prevents the liquid from entering sheet member 71 from the outer circumferential side to the inner circumferential side.

The upper end of coupling shaft 65 projects upward relative to pressing member 72 fixed to liquid medication bottle holder 32. A disc-like circular connector 74 is fixed to the upper end of coupling shaft 65. Circular connector 74 has formed therein a fixing hole 74a on the side closer to the center and a fixing hole 74b on the side closer to the periphery. Circular connector 74 and coupling shaft 65 are fixed integrally by inserting a bolt through fixing hole 74a.

A cover 75 is provided so as to cover circular connector 74 and pressing member 72. Circular connector 74 and cover 75 are fixed integrally by inserting a bolt through fixing hole 74b on the peripheral side of the circular connector and a fixing hole 75b formed in cover 75. Cover 75 has a disc portion to be brought into contact with the upper surface of circular connector 74 and a cylindrical portion projecting from the periphery of this disc portion toward liquid medication bottle holder 32. Cylindrical portion is larger in diameter than circular connector 74 and pressing member 72, and the outer circumferential surface of pressing member 72 is surrounded by the cylindrical portion. The disc portion of cover 75 is in surface contact with circular connector 74.

With the waterproof structure as described above, a liquid, if spilled on cover 75 from above, flows from the disc portion of cover 75 to the outer side of the cylindrical portion, and the liquid is prevented from flowing toward pressing member 72 on the radially inner side. Since the liquid is prevented from flowing to the inner side of pressing member 72, the liquid is prevented from reaching shaft 64 beyond pressing member 72 and sheet member 71. Moreover, even if the liquid flows via fixing holes 75b, 74b for fixing cover 75 and circular connector 74, the liquid is prevented from reaching fixing hole 74a in the vicinity of the center of circular connector 74 since fixing hole 74b is formed in the vicinity of the outer circumference of circular connector 74, which prevents the liquid from reaching shaft 64 via fixing hole 74a. Therefore, the occurrence of flow of liquid along shaft 64 can be prevented, and liquid medication 5 can be prevented from entering motor 62 along shaft 64.

Moreover, by removably attaching each element forming the waterproof structure described above by means of a bolt, for example, liquid medication 5, if spilled, can be cleaned easily by removing each element.

A disc-like cup fixing part 76 is fixed on the upper side of cover 75. A projection 77 projecting upward is formed in cup fixing part 76. This projection 77 is fitted within a recess formed in the bottom surface of cup 78, so that cup 78 can be positioned relative to cup fixing part 76, which can prevent cup 78 from being displaced. Cup fixing part 76 is made of a ferromagnetic material. Therefore, by placing a magnet on the bottom surface of cup 78, cup 78 magnetically adheres to cup fixing part 76 and is fixed thereto. With such a structure, merely by locating cup 78 in alignment with projection 77 to be mounted on cup fixing part 76, cup 78 can be easily fixed while being appropriately positioned relative to cup fixing part 76.

A nonslip sheet not shown is bonded to the inner bottom surface of cup 78 opposed to bottom 23B of liquid medication bottle 23. This nonslip sheet prevents liquid medication bottle 23 from slipping over the inner bottom surface of cup 78, and enables liquid medication bottle 23 to switch the direction of rotation smoothly together with cup 78 when a switch is made between the forward rotation and reverse rotation of rotationally driving unit 61.

Figure 12:
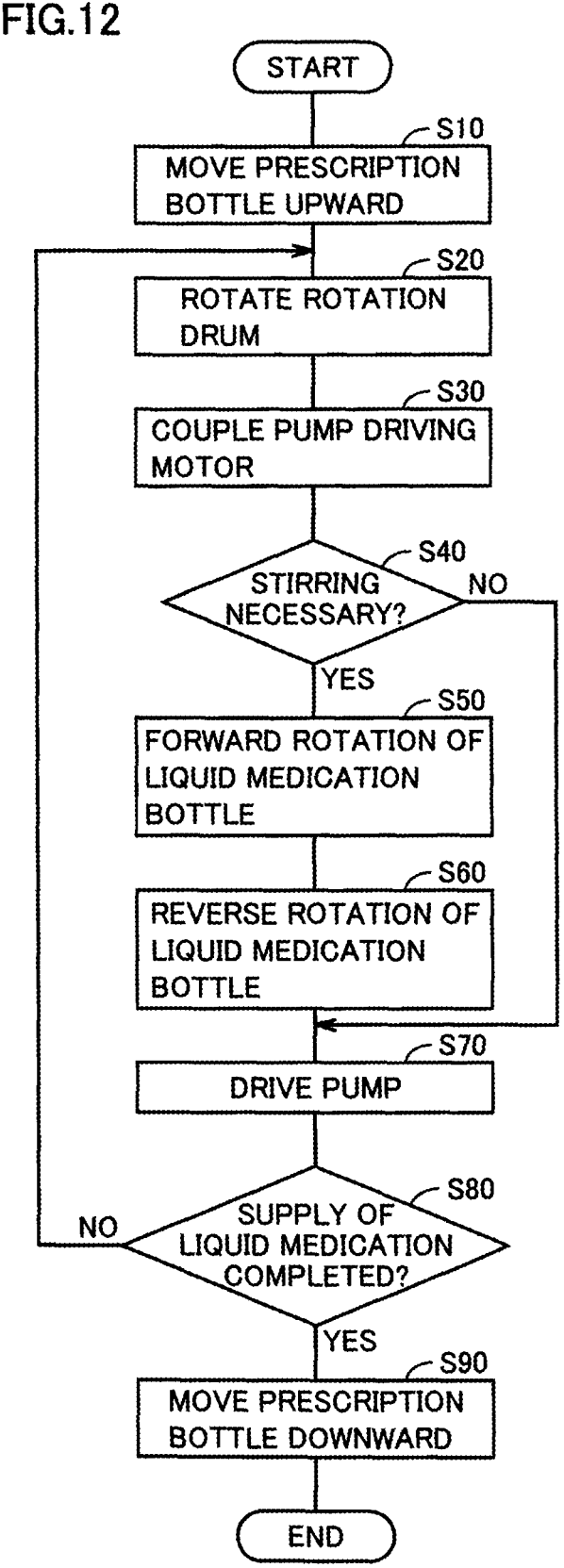
FIG. 12 is a flow chart showing an example of a control method of the liquid medication dispensing machine.

Control exerted when supplying liquid medication 5 from liquid medication bottle 23 to prescription bottle 2 for dispensing will now be described. FIG. 12 is a flow chart showing an example of a control method of liquid medication dispensing machine 1.

First, when prescription bottle 2 is set on table 48 located at the initial position where prescription bottle 2 is placed on table 48, and touch panel 14 is operated to issue a command to start supply of liquid medication 5 to prescription bottle 2, then, as shown in a step (S10), a control signal is transmitted to elevating device 50. When elevating device 50 moves weight detection unit 4 upward, prescription bottle 2 is moved upward. Weight detection unit 4 is moved upward until it reaches the supply position where liquid medication 5 is supplied to prescription bottle 2.

Next, in a step (S20), drum rotating motor 22 is controlled, and rotation drum 21 is rotated. In the initial state prior to conducting dispensing by liquid medication dispensing machine 1, supply port 36A formed at the lower end of supply nozzle 36 is not located at a position facing opening 2A formed at the upper end of prescription bottle 2, but prescription bottle 2 is located between supply nozzles 36, 36 adjacent to each other in the circumferential direction. When drum rotating motor 22 is driven, rotation drum 21 is rotated such that supply nozzle 36 is moved horizontally to the position where supply port 36A of supply nozzle 36 faces opening 2A of prescription bottle 2.

At this time, liquid medication bottle 23 mounted on liquid medication bottle holder 32 attached to rotation drum 21 is also moved horizontally. Then, liquid medication bottle 23 from which liquid medication 5 contained therein is discharged is located on the forefront side of liquid medication dispensing machine 1. Since liquid medication bottle 23 is moved in this way, the type of liquid medication 5 dispensed can be visually identified from the front of liquid medication dispensing machine 1.

When the rotation of rotation drum 21 is completed, then, in a step (S30), pump driving motor 40 is moved forward, and coupling member 42 of pump driving motor 40 is coupled to coupled member 44 of pump 24. This brings about the state where rotation of pump driving motor 40 can be transmitted to pump 24, that is, the state where pump 24 can be driven.

Next, in a step (S40), it is determined whether or not liquid medication 5 to be supplied to prescription bottle 2 is liquid medication 5 of the type that requires stirring. If it is determined that stirring is necessary, subsequently in a step (S50), rotationally driving unit 61 is driven in the forward direction, so that liquid medication bottle 23 is rotated in the forward direction. Furthermore, in a step (S60), rotationally driving unit 61 is driven in the reverse direction, so that liquid medication bottle 23 is rotated in the reverse direction. Liquid medication 5 in liquid medication bottle 23 is sufficiently stirred by this forward and reverse rotation of liquid medication bottle 23.

Then, in a step (S70), pump 24 is driven to supply a predetermined quantity of liquid medication 5 in liquid medication bottle 23 to prescription bottle 2 via tube 34 and supply nozzle 36. By supplying liquid medication 5 to prescription bottle 2 after rotationally driving unit 61 rotates liquid medication bottle 23, liquid medication 5 having been sufficiently stirred can be supplied. Therefore, liquid medication 5 of the type that requires stirring prior to dispensing in accordance with the prescription guidelines can be dispensed automatically using liquid medication dispensing machine 1 of the present embodiment.

If it is determined that stirring is unnecessary in step (S40), the step of rotating liquid medication bottle 23 is skipped, and pump 24 is driven immediately to supply liquid medication 5 from liquid medication bottle 23 to prescription bottle 2. Liquid medication bottle 23 containing liquid medication 5 which does not require stirring is held inside cup 78 attached to the upper surface of liquid medication bottle holder 32 with cup fixing part 76A (see FIGS. 6 to 10) interposed therebetween. Rotationally driving unit 61 is not provided under cup fixing part 76A.

Then, in a step (S80), it is determined whether or not supply of liquid medication 5 (and a diluent if necessary) to prescription bottle 2 has been fully completed and dispensing has been completed. If supply of liquid medication 5 has not been completed, the process is returned to step (S20), and rotation drum 21 is rotated such that liquid medication bottle 23 containing liquid medication 5 to be supplied next is located on the forefront side of the device. When supply of liquid medication 5 has been completed, elevating device 50 moves table 48 downward, so that prescription bottle 2 is moved downward. Table 48 is moved downward until it returns to the initial position from the supply position. The supply of liquid medication 5 to prescription bottle 2 through the use of liquid medication dispensing machine 1 of the present embodiment is thereby completed.

Figure 13:
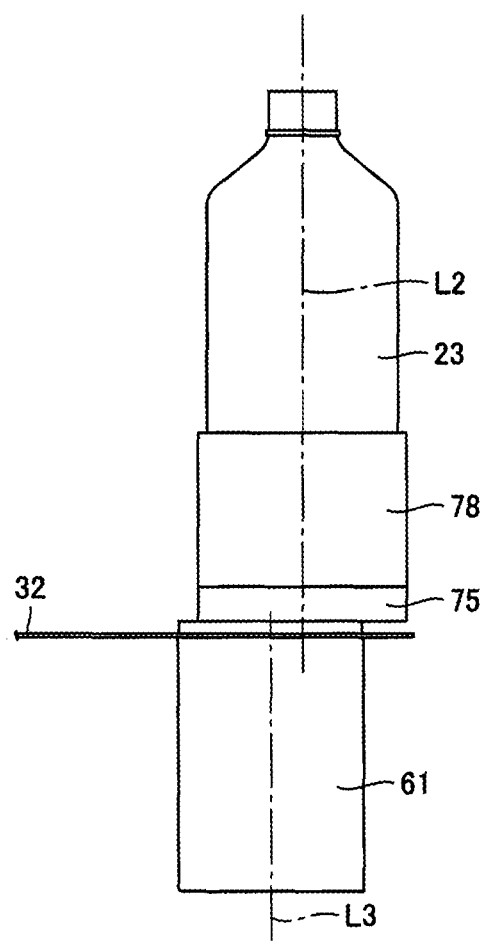
FIG. 13 is a schematic diagram showing a variation of a stirring device.

FIG. 13 is a schematic diagram showing a variation of a stirring device. In the example shown in FIG. 13, center line L2 of liquid medication bottle 23 is offset from rotation axis L3 of rotationally driving unit 61, and cup 78 as a holder holds liquid medication bottle 23 with center line L2 displaced from rotation axis L3.

In order to easily store liquid medication bottle 23 in cup 78, the diameter of cup 78 is formed somewhat larger than the diameter of liquid medication bottle 23, and there is some room between liquid medication bottle 23 and cup 78. Therefore, it is considered that center line L2 and rotation axis L3 actually do not match completely in the structure shown in FIG. 8 as well, and liquid medication 5 in liquid medication bottle 23 is eccentrically rotated relative to the rotation of rotationally driving unit 61. Liquid medication 5 is efficiently stirred by this eccentric rotation. Then, with the structure where center line L2 and rotation axis L3 are intentionally offset as shown in FIG. 13, liquid medication 5 in liquid medication bottle 23 is reliably rotated eccentrically relative to the rotation of rotationally driving unit 61, and the degree of eccentricity can be increased, so that liquid medication 5 can be stirred much more efficiently.

Figure 14:
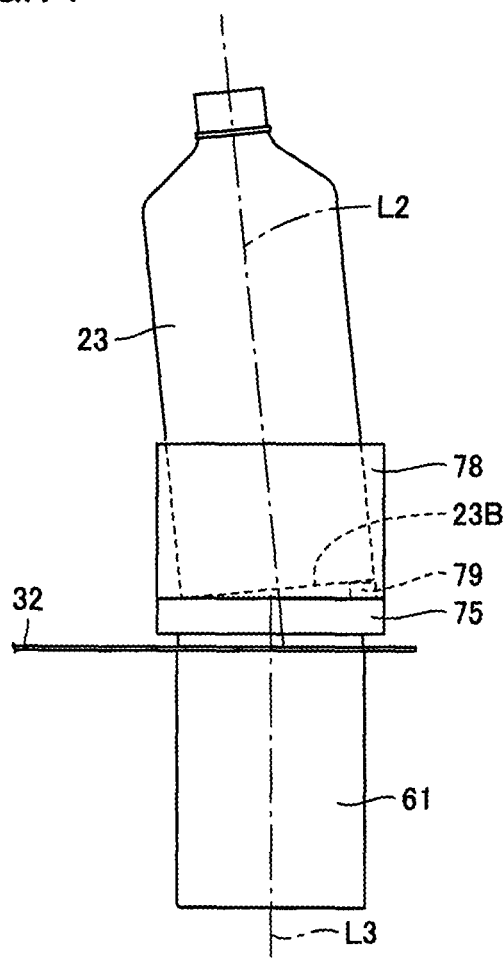
FIG. 14 is a schematic diagram showing another variation of a stirring device.

FIG. 14 is a schematic diagram showing another variation of a stirring device. In the example shown in FIG. 14, a projection 79 projecting upward is provided on the bottom surface of cup 78, and liquid medication bottle 23 is located in cup 78 such that bottom 23B of liquid medication bottle 23 rests upon projection 79. Then, center line L2 of liquid medication bottle 23 can be inclined with respect to rotation axis L3 of rotationally driving unit 61, and the rotation axis of liquid medication 5 in liquid medication bottle 23 is also inclined with respect to rotation axis L3. By thus offsetting the rotation axis, liquid medication 5 can be stirred much more efficiently.

Second Embodiment

Figure 15:
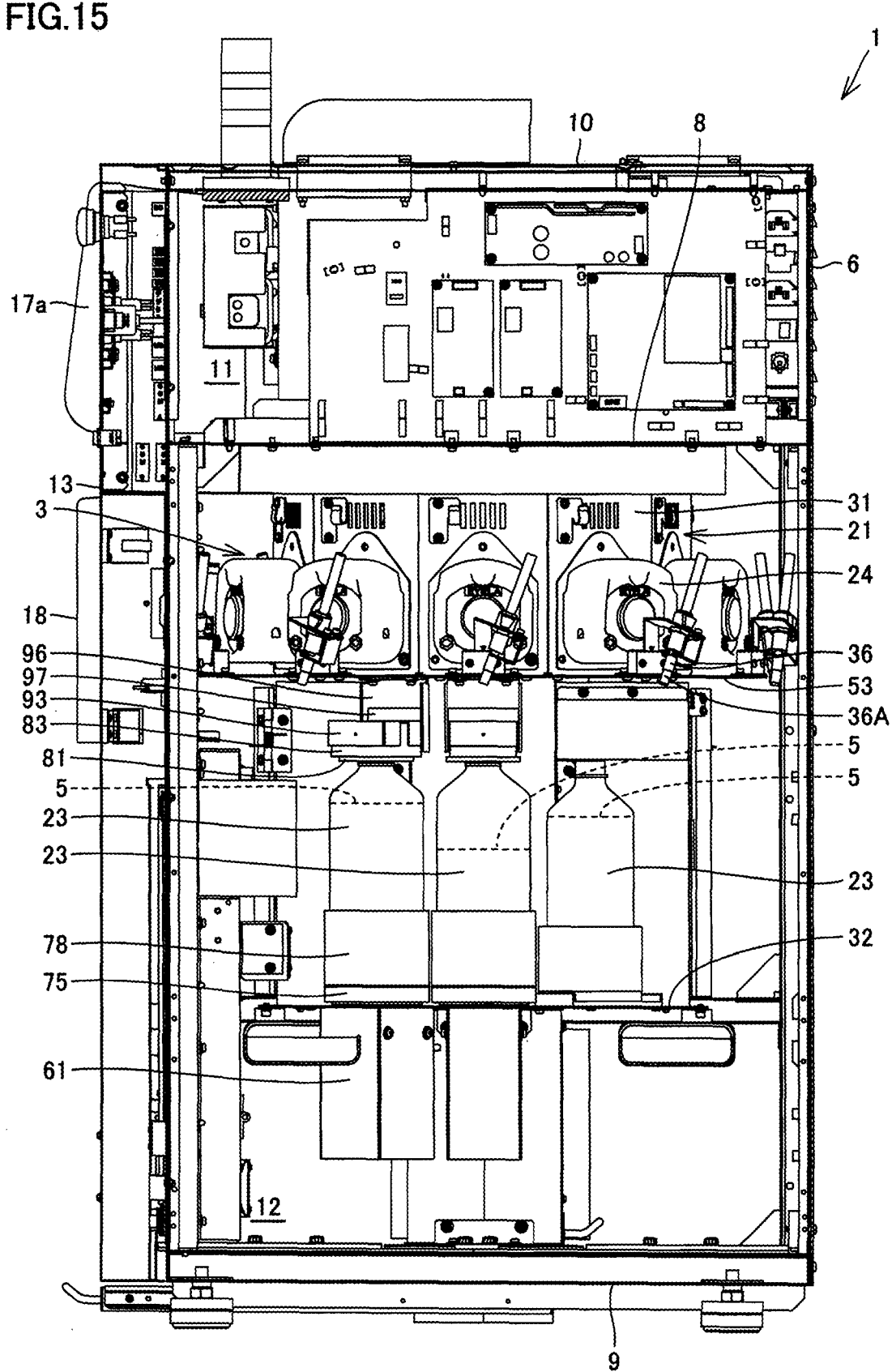
FIG. 15 is a cross sectional view of a liquid medication dispensing machine of a second embodiment.
Figure 16:
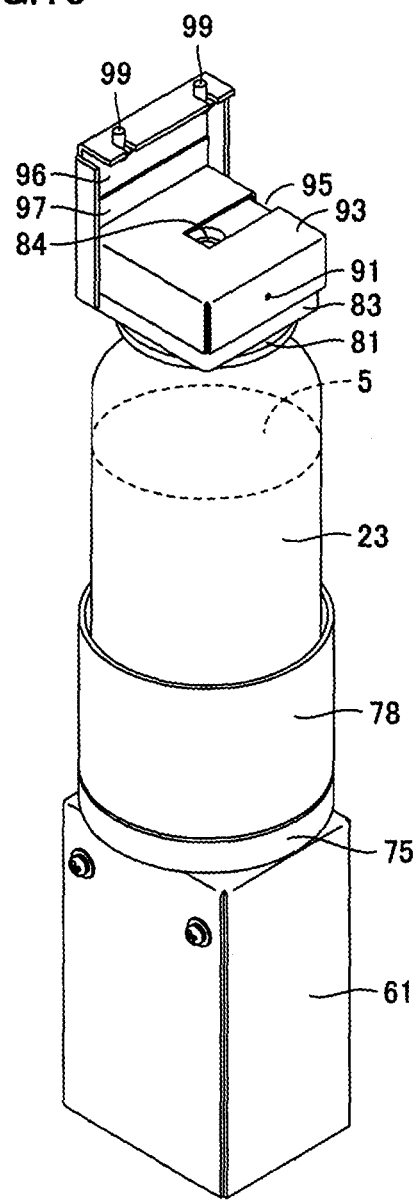
FIG. 16 is a perspective view showing a structure of a tube holding structure of the second embodiment.
Figure 17:
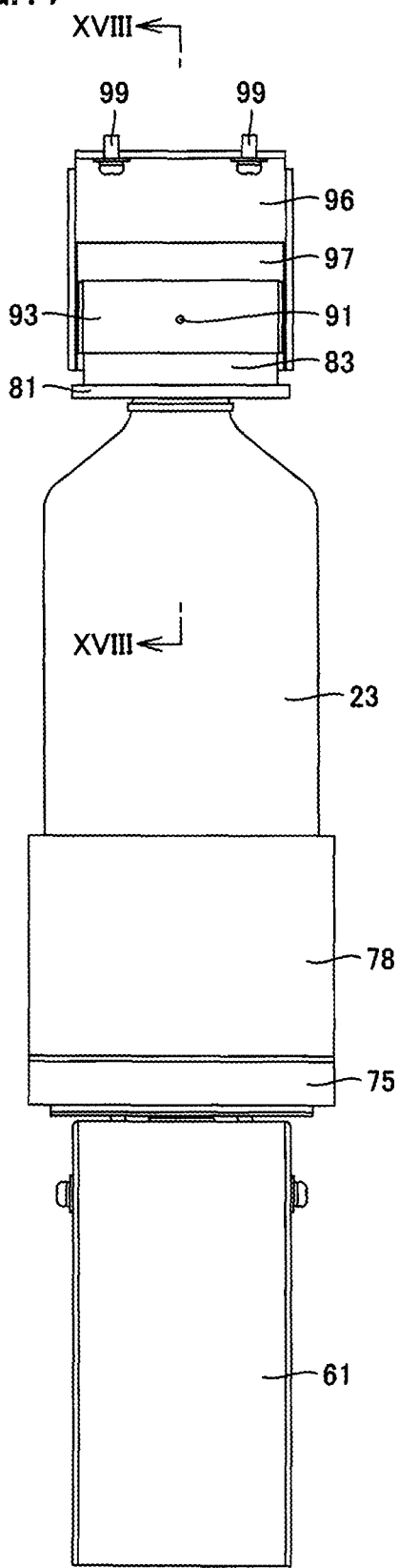
FIG. 17 is a side view of the tube holding structure shown in FIG. 16.
Figure 18:
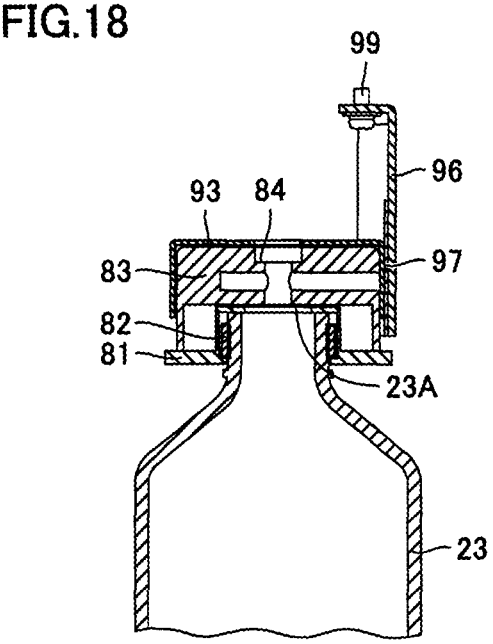
FIG. 18 is a cross sectional view of the tube holding structure taken along the line XVIII-XVIII shown in FIG. 17.
Figure 19:
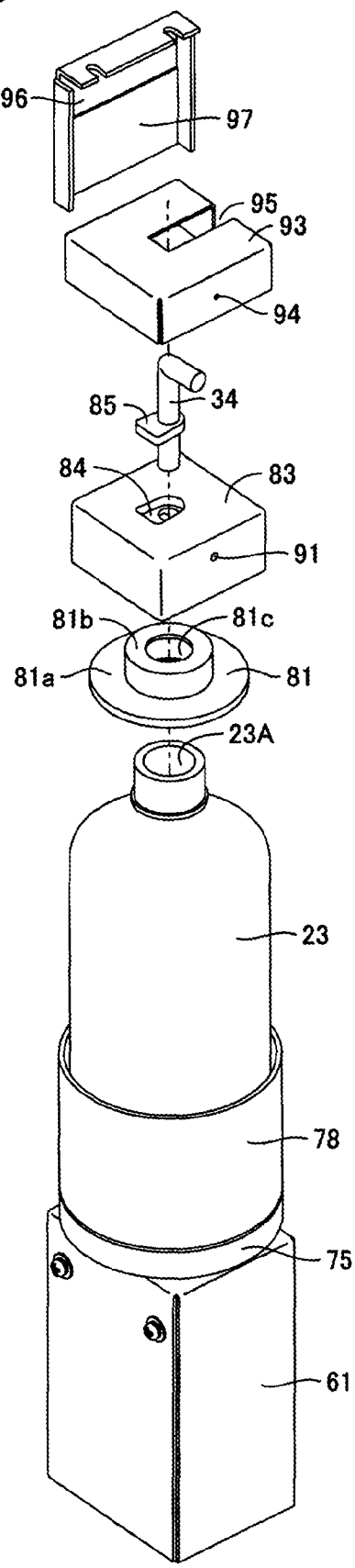
FIG. 19 is an exploded perspective view of the tube holding structure of the second embodiment.

FIG. 15 is a cross sectional view of a liquid medication dispensing machine of a second embodiment. FIG. 16 is a perspective view showing a structure of a tube holding structure of the second embodiment. FIG. 17 is a side view of the tube holding structure shown in FIG. 16. FIG. 18 is a cross sectional view of the tube holding structure taken along the line XVIII-XVIII shown in FIG. 17. FIG. 19 is an exploded perspective view of the tube holding structure of the second embodiment. The liquid medication dispensing machine of the second embodiment differs from that of the first embodiment in the structure of the tube holding structure holding tube 34 in opening 23A of liquid medication bottle 23.

Base member 81 has a structure similar to that of the first embodiment, and has annular disc-like flange portion 81a and cylindrical sleeve portion 81b projecting from the upper surface of flange portion 81a. Base member 81 is fixed to opening 23A of liquid medication bottle 23 with elastically deformable spacer 82 interposed therebetween. Different from the first embodiment, cover 83 has an approximately rectangular box-like cap shape having a rectangular frame-like wall portion and a rectangular plate-like top portion covering the upper end of the wall portion. Cover 83 is mounted on the upper surface of flange portion 81a while not being fixed to base member 81. Cover 83 is provided to cover opening 23A of liquid medication bottle 23 with cover 83 mounted on base member 81.

A metal cover 93 is located so as to cover the outer surface of the wall portion and the upper surface of the top portion of cover 83. Metal cover 93 has an approximately rectangular box-like shape similarly to cover 83. A small projection 91 is provided on the outer surface of the wall portion of cover 83, and a small hole 94 extending through the wall portion is formed in the wall portion of metal cover 93. When small projection 91 is fitted within small hole 94, metal cover 93 is assembled to cover 83 so as to cover the outer surface of cover 83.

Tube 34 is attached to cover 83 by fitting positioning member 85 attached to tube 34 into recess 84. Metal cover 93 is put over cover 83 after tube 34 is attached to cover 83, and is assembled integrally with cover 83. Metal cover 93 has formed therein a cutout 95 extending from the outer edge to the central part of metal cover 93. Tube 34 is located to pass through cutout 95, move relatively with respect to metal cover 93, and extend through metal cover 93 at the central part of metal cover 93.

When metal cover 93 is assembled to cover 83, metal cover 93 covers part of recess 84 formed in cover 83. When metal cover 93 is assembled to cover 83 with tube 34 attached to cover 83, metal cover 93 is located to cover positioning member 85 received in recess 84. Positioning member 85 is kept received in recess 84 by metal cover 93. Metal cover 93 prevents positioning member 85 from moving in the longitudinal direction of tube 34, and prevents positioning member 85 from being removed from recess 84. Since metal cover 93 prevents positioning member 85 from moving, cover 83, positioning member 85 and metal cover 93 position tube 34 in the longitudinal direction of tube 34.

An attaching member 96 is fixed on the lower surface side of nozzle attachment plate 53 instead of tube fixing part 86 of the first embodiment. Attaching member 96 is formed so as to be capable of receiving one surface of the wall portion of approximately rectangular box-like metal cover 93. Attaching member 96 is fixed to nozzle attachment plate 53 by means of a fixture 99, such as a bolt or a pin. Tube 34 is attached to cover 83 with positioning member 85 interposed therebetween, extends from cover 83 to the main body of liquid medication dispensing machine 1, and is engaged with cutout 54 formed in nozzle attachment plate 53 to be fixed to nozzle attachment plate 53.

Metal cover 93 is made of a ferromagnetic metal material. A magnet 97 is assembled to attaching member 96. Magnet 97 has a flat plate-like shape such that ferromagnetic metal cover 93 can magnetically adhere thereto. As clearly shown in FIGS. 16 and 18, metal cover 93 is fixed to attaching member 96 by causing one surface of the wall portion of metal cover 93 to magnetically adhere to magnet 97. That is, metal cover 93 is fixed to attaching member 96 with magnet 97 interposed therebetween, and is thereby fixed to nozzle attachment plate 53 on the main body side of liquid medication dispensing machine 1.

The positioning unit of the second embodiment further includes metal cover 93 in addition to base member 81, cover 83 and positioning member 85. The positioning unit includes metal cover 93 as a magnetic component magnetically adhering to magnet 97 fixed to nozzle attachment plate 53 on the main body side of liquid medication dispensing machine 1 with attaching member 96 interposed therebetween. Tube 34 is attached to liquid medication bottle 23 with this positioning unit interposed therebetween. Such a positioning unit can attach tube 34 to liquid medication bottle 23 such that tube 34 is relatively rotated with respect to liquid medication bottle 23 and positioned relative to liquid medication bottle 23 so as to pass through the central part of opening 23A.

By fixing attaching member 96 to nozzle attachment plate 53 with fixture 99 interposed therebetween, the positioning unit is attached to nozzle attachment plate 53 on the main body side of liquid medication dispensing machine 1 at a position where opening 23A of liquid medication bottle 23 is covered. Metal cover 93 included in the positioning unit is attached to magnet 97 by magnetic force, and is removably attached to attaching member 96 fixed to nozzle attachment plate 53 on the main body side of liquid medication dispensing machine 1.

In the second embodiment, since cover 83 can be fixed to the main body of liquid medication dispensing machine 1 using magnet 97 and metal cover 93, misalignment of cover 83 and base member 81 in the horizontal direction can be prevented. Therefore, tube 34 with positioning member 85 fitted within recess 84 of cover 83 can be prevented from moving horizontally along with misalignment of cover 83. Therefore, tube 34 fixed to nozzle attachment plate 53 at cutout 54 can be prevented from sliding over nozzle attachment plate 53, and the outer surface of tube 34 can be prevented from being worn out.

Moreover, by holding positioning member 85 between cover 83 and metal cover 93, positioning member 85 is kept inside recess 84, and positioning member 85 can be prevented from being removed from recess 84. Therefore, positioning member 85 can be prevented from being removed from cover 83, and tube 34 can be prevented from sliding over cover 83 or nozzle attachment plate 53 to be worn out.

The characteristic structure of the tube holding structure of the second embodiment described above is summarized below. That is, the tube holding structure according to the second embodiment is a tube holding structure used for liquid medication dispensing machine 1 for supplying liquid medication 5 from liquid medication bottle 23 containing liquid medication 5 to prescription bottle 2, the tube holding structure holding tube 34 through which liquid medication 5 flown out of liquid medication bottle 23 passes. Liquid medication bottle 23 is provided rotatably around the rotation axis along center line L2 of liquid medication bottle 23. The outer diameter of tube 34 is formed smaller than the diameter of opening 23A of liquid medication bottle 23. The tube holding structure includes the positioning unit that positions tube 34 relative to liquid medication bottle 23 so as to pass through the central part of opening 23A, thereby attaching tube 34 to liquid medication bottle 23.

Then, tube 34 can be prevented from contacting opening 23A and can be prevented from being rotated together with liquid medication bottle 23 while liquid medication bottle 23 is being rotated. Therefore, the occurrence of twist of tube 34 can be prevented, and the occurrence of a problem, such as removal of tube 34 from liquid medication bottle 23, falling of liquid medication bottle 23 or damage to tube 34, can be prevented. It is also possible to prevent tube 34 from contacting rotating liquid medication bottle 23 and base member 81 and to prevent the outer surface of tube 34 from being worn out. Therefore, damage to tube 34 can be prevented, and wear debris of tube 34 can be prevented from entering liquid medication bottle 23.

Moreover, the positioning unit is located at the position covering opening 23A. The positioning unit is attached to nozzle attachment plate 53 on the main body side of liquid medication dispensing machine 1 by assembling attaching member 96 fixed to nozzle attachment plate 53 and metal cover 93 included in the positioning unit with magnet 97 interposed therebetween.

Tube 34 positioned relative to liquid medication bottle 23 by the positioning unit can be prevented from becoming misaligned with the main body of liquid medication dispensing machine 1 with the positioning unit attached to the main body of liquid medication dispensing machine 1. Therefore, tube 34 can be prevented from becoming misaligned with liquid medication bottle 23 held by liquid medication bottle holder 32 on the main body side of liquid medication dispensing machine 1, and tube 34 can thus be prevented from being unintentionally worn out. Tube 34 can be positioned relative to liquid medication bottle 23 more reliably by locating the positioning unit at the position where opening 23A of liquid medication bottle 23 is covered and attaching the positioning unit to the main body of liquid medication dispensing machine 1 in the vicinity of opening 23A.

Moreover, the positioning unit includes cover 83 formed with recess 84 into which positioning member 85 is fitted and metal cover 93 covering cover 83 from the outside. With metal cover 93 covering positioning member 85 received in recess 84, positioning member 85 is held between cover 83 and metal cover 93 in the longitudinal direction of tube 34. Then, positioning member 85 is prevented from moving in the longitudinal direction of tube 34, and positioning member 85 can thus be prevented from moving upward relative to cover 83 to be removed from recess 84. Therefore, positioning member 85 can be prevented from being removed from cover 83, and tube 34 can be prevented from sliding over cover 83 or nozzle attachment plate 53 to be worn out.

Moreover, the positioning unit includes metal cover 93 magnetically adhering to magnet 97 fixed to the main body of liquid medication dispensing machine 1. Then, by providing magnet 97 fixed integrally to the main body side of liquid medication dispensing machine 1 and bringing ferromagnetic metal cover 93 into contact with magnet 97, metal cover 93 can be easily fixed to the main body side of liquid medication dispensing machine 1.

Since metal cover 93 and cover 83 both have a rectangular box-like shape, and small projection 91 is fitted within small hole 94 to be assembled integrally so that the amount of relative movement in the horizontal direction is small, cover 83 is also fixed along with fixing of metal cover 93. Cover 83 can therefore be prevented from becoming misaligned with base member 81. Tube 34 can therefore be prevented from becoming misaligned with base member 81 together with cover 83. In addition, since metal cover 93 has the form covering part of recess 84 formed in cover 83, positioning member 85 is held between metal cover 93 and cover 83 by assembling metal cover 93 to cover 83. Tube 34 can therefore be prevented by metal cover 93 from being moved in the longitudinal direction. Tube 34 can therefore be positioned more reliably.

The positioning unit is removably attached to the main body of liquid medication dispensing machine 1. Then, the positioning unit can be attached to the main body of liquid medication dispensing machine 1 after fitting positioning member 85 into recess 84 of cover 83 constituting the positioning unit, putting metal cover 93 over cover 83 for assembly with small projection 91 and small hole 94 aligned with each other, and assembling the positioning unit integrally. The ease of assembly of the positioning unit can thereby be improved. Since the positioning unit can be attached to the main body of liquid medication dispensing machine 1 by magnetic force in an easy operation of bringing metal cover 93 included in the positioning unit into contact with magnet 97, the positioning unit can be attached more easily.

Because magnet 97 has a flat plate-like shape, the outer surface of the wall portion of rectangular box-like metal cover 93 is brought into surface contact with magnet 97, and the strength by which metal cover 93 magnetically adheres to magnet 97 can be increased. Moreover, metal cover 93 can magnetically adhere to an arbitrary position of planar magnet 97, and as a result, in the case where liquid medication bottles 23 differ in height, metal cover 93 located depending on the heights of liquid medication bottles 23 can reliably magnetically adhere to magnet 97.

Although the embodiments of the present invention have been described above, it should be understood that the embodiments disclosed herein are illustrative and non-restrictive in every respect. The scope of the present invention is defined by the claims not by the description above, and is intended to include any modification within the meaning and scope equivalent to the terms of the claims.

REFERENCE SIGNS LIST 1 liquid medication dispensing machine; 2 prescription bottle; 2A opening; 5 liquid medication; 6 housing; 21 rotation drum; 23 liquid medication bottle; 23A opening; 23B bottom; 24 pump; 32 liquid medication bottle holder; 34 tube; 34a one end; 34b the other end; 36 supply nozzle; 36A supply port; 53 nozzle attachment plate; 54 cutout; 61 rotationally driving unit; 62 motor; 64 shaft; 65 coupling shaft; 71 sheet member; 72 pressing member; 73 fixing member; 74 circular connector; 74a, 74b, 75b fixing hole; 75 cover; 76, 76A cup fixing part; 77 projection; 78 cup; 81 base member; 81a flange portion; 81b sleeve portion; 81c through-hole; 82 spacer; 83 cover; 84 recess; 85 positioning member; 86 tube fixing part; 93 metal cover; 95 cutout; 96 attaching member; 97 magnet.

The invention claimed is:

1. A liquid medication dispensing machine supplying a liquid medication from at least one of a plurality of liquid medication bottles containing said liquid medication to a prescription bottle, the plurality of liquid medication bottles including a first liquid medication bottle and a second liquid medication bottle, said liquid medication dispensing machine comprising:
a rotationally driving unit generating rotary force and rotating at least one of said liquid medication bottles around a rotation axis extending through a bottom of said at least one liquid medication bottle,
wherein a rotation of said first liquid medication bottle is independent of a rotation of said second liquid medication bottle.

2. The liquid medication dispensing machine according to claim 1, comprising a tube through which said liquid medication flowing out of said at least one liquid medication bottle passes, wherein
said tube is located inside said at least one liquid medication bottle and extends from the opening toward said bottom of said at least one liquid medication bottle.

3. The liquid medication dispensing machine according to claim 1, wherein a holder holds said at least one liquid medication bottle with a center line of said at least one liquid medication bottle displaced from said rotation axis.

4. The liquid medication dispensing machine according to claim 1, wherein said rotationally driving unit generates the rotary force both in forward and reverse directions, and rotates said at least one liquid medication bottle in the forward direction and then rotates said at least one liquid medication bottle in the reverse direction opposite to said forward direction.

5. The liquid medication dispensing machine according to claim 1, wherein said liquid medication is supplied to said prescription bottle after said rotationally driving unit rotates said at least one liquid medication bottle.

6. The liquid medication dispensing machine according to claim 1, comprising:
a tube through which said liquid medication flowing out of said at least one liquid medication bottle passes; and
a positioning unit positioning said tube relative to said at least one liquid medication bottle such that said tube passes through a central part of an opening of said at least one liquid medication bottle, wherein
an outer diameter of said tube is formed smaller than a diameter of said opening, and said tube is attached to said at least one liquid medication bottle with said positioning unit interposed therebetween.

7. The liquid medication dispensing machine according to claim 6, wherein said positioning unit attaches said tube to said at least one liquid medication bottle such that said tube is relatively rotated with respect to said at least one liquid medication bottle.

8. The liquid medication dispensing machine according to claim 6, wherein said positioning unit is attached to a main body of said liquid medication dispensing machine.

9. The liquid medication dispensing machine according to claim 8, wherein said positioning unit is removably attached to said main body of said liquid medication dispensing machine.

10. The liquid medication dispensing machine according to claim 6, wherein
said tube includes one end located inside said at least one liquid medication bottle and a positioning member attached to said tube at a predetermined distance from said one end, and
said tube is positioned relative to said at least one liquid medication bottle by said positioning member being held by said positioning unit.

11. The liquid medication dispensing machine according to claim 10, wherein said positioning member prevents said tube from being rotated relative to said positioning unit.

12. The liquid medication dispensing machine according to claim 10, wherein said positioning unit holds said positioning member in a longitudinal direction of said tube.

13. The liquid medication dispensing machine according to claim 6, wherein
a base member rotating integrally with said at least one liquid medication bottle is fixed to said opening,
said positioning unit includes a cover mounted on said base member while covering said opening and not rotated while said at least one liquid medication bottle is being rotated but sliding over said base member, and
said tube is engaged with said cover to be positioned relative to said at least one liquid medication bottle.

14. The liquid medication dispensing machine according to claim 1, wherein an axis of rotation of said rotationally driving unit is substantially coaxial with said rotation axis of said at least one liquid medication bottle.

15. The liquid medication dispensing machine according to claim 1, wherein said at least one liquid medication bottle contains said liquid medication which needs stirring.

16. The liquid medication dispensing machine according to claim 1, wherein the liquid medication dispensing machine comprises at least one holder holding said bottom of said at least one liquid medication bottle,
wherein said rotationally driving unit rotates said at least one holder and said at least one liquid medication bottle held by said at least one holder.

* * * * *